(12) United States Patent
Okamoto et al.

(10) Patent No.: US 6,476,215 B1
(45) Date of Patent: Nov. 5, 2002

(54) INK JET METHOD OF SPOTTING A PROBE AND MANUFACTURING A PROBE ARRAY

(75) Inventors: Tadashi Okamoto, Yokohama (JP); Nobuko Yamamoto, Isehara (JP); Tomohiro Suzuki, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/126,851

(22) Filed: Jul. 31, 1998

(30) Foreign Application Priority Data

| Aug. 1, 1997 | (JP) | ................................................ 9-207837 |
| Oct. 20, 1997 | (JP) | ................................................ 9-287046 |
| Jul. 24, 1998 | (JP) | ............................................ 10-209923 |

(51) Int. Cl.⁷ .................... C07H 21/00; G01N 15/00; G01N 33/53; C12Q 1/68; C07K 17/00
(52) U.S. Cl. .................... 536/25.3; 422/50; 422/68.1; 435/6; 435/7.1; 436/501; 530/333
(58) Field of Search .................... 435/6, 7.1; 436/501; 536/25.3; 530/333; 422/50, 68.1

(56) References Cited

U.S. PATENT DOCUMENTS

| 4,775,619 A | * 10/1988 | Urdea ........................... 435/6 |
| 5,108,926 A | 4/1992 | Klebe ........................... 435/284 |
| 5,143,854 A | 9/1992 | Pirrung et al. .............. 436/518 |
| 5,202,231 A | 4/1993 | Drmanac et al. ............ 435/6 |
| 5,324,650 A | 6/1994 | Obzansky et al. .......... 435/188 |
| 5,405,783 A | 4/1995 | Pirrung et al. .............. 436/518 |
| 5,424,186 A | 6/1995 | Fodor et al. .................... 435/6 |
| 5,474,796 A | 12/1995 | Brennan ..................... 427/2.13 |
| 5,601,980 A | 2/1997 | Gordon et al. ................ 435/6 |
| 5,688,642 A | 11/1997 | Chrisey et al. ............... 435/6 |
| 5,847,105 A | * 12/1998 | Baldeschwieler et al. .. 536/25.3 |
| 5,958,342 A | * 9/1999 | Gamble et al. ............. 422/100 |
| 6,001,309 A | * 12/1999 | Gamble et al. ............. 422/100 |
| 6,015,880 A | * 1/2000 | Baldeschwieler et al. ... 530/333 |
| 6,057,100 A | * 5/2000 | Heyneker ....................... 435/6 |
| 6,083,763 A | * 7/2000 | Balch ........................... 436/518 |
| 6,312,960 B1 | * 11/2001 | Balch et al. ................. 436/518 |

FOREIGN PATENT DOCUMENTS

| EP | 0373203 | 8/1994 |
| JP | 04-359072 | 12/1992 |
| JP | 06-066799 | 3/1994 |
| JP | 09-054093 | 2/1997 |
| WO | WO 86/05518 | * 9/1986 |
| WO | WO89-10977 | 11/1989 |
| WO | WO93-22678 | 11/1993 |
| WO | WO95-25116 | 9/1995 |
| WO | WO95/35505 | 12/1995 |

OTHER PUBLICATIONS

J. DNA Seq. & Map. 1; 375–388, 1991.
Nucleic Acids Research, vol. 24, No. 15, 1996, pp. 3040–3047.

(List continued on next page.)

Primary Examiner—Ardin H. Marschel
(74) Attorney, Agent, or Firm—Fitzpatrick, Cella, Harper & Scinto

(57) ABSTRACT

Provided is a method of spotting a probe densely and efficiently on a surface of a solid support. A liquid containing a probe is attached to a solid support as droplets to form spots containing the probe on the solid support by an ink jet method.

16 Claims, 4 Drawing Sheets

OTHER PUBLICATIONS

Anal. Chem., vol. 69, No. 4, Feb. 1997, pp. 543–551.

Nucleic Acids Research, 1996, vol. 24 (15), pp. 3031–3039.

Chem. Pharm. Bull. vol. 29, No. 4 (1981) pp. 130–1135.

Patent Abstracts of Japan, Public. No. 06066799, Public. Date Mar. 11, 1994, Teruuchi Toshiyuki, "Measuring Methof For Antgen".

Patent Abstracts of Japan, Public. No. 07179797, Public. Date Jul. 18, 1995, Kubota Hidemi, "Bubble Jet Recording Liquid And Recording Method Using The Same".

Patent Abstracts of Japan, Public. No. 59021391, Public. Date Feb. 3, 1984, Etani Hajime, "Glass For Immobilization And Its Preparation".

Patent Abstracts of Japan, Public. No. 09054093, Public. Date Feb. 25, 1997, Takayama Katsuyoshi, "Method For Putting Antigen Or Antibody Into Solid Phase".

Derment Database, AN 93–031735, XP002105850, JP04359072A, (Seiko Epson Corp.), Dec. 11, 1992 (abstract).

Mark Schena et al., "Quantitative Monitoring of Gene Expression Patterns with a Complementary DNA Microarray", Science, vol. 270, pp. 467–470, Oct. 20, 1995.

O'Donnel–Maloney, et al., "Microfabrication and array technologies for DNA sequencing and diagnostics", Genetic Analysis: Biomolecular Engineering, vol. 13 (1996), pp. 151–157.

Chrisey, et al., "Fabrication of patterned DNA surfaces", Nucleic Acids Research vol. 24, No. 15 (1996), pp. 3040–3047.

* cited by examiner

INK JET METHOD OF SPOTTING A PROBE AND MANUFACTURING A PROBE ARRAY

BACKGROUND OF THE INVENTION

1. Field of the Invention

The present invention relates to a method of spotting a probe on a solid support, a probe array and a method of manufacturing thereof, and a method of detecting a target single-stranded (ss) nucleic acid and a method of identifying a base sequence of a target ss nucleic acid using the probe array.

2. Related Background Art

As a method to determine a base sequence of a nucleic acid, detect a target nucleic acid in a sample, and identify various bacteria swiftly and accurately, proposed is the use of a probe array where one or more substances which can bind specifically to a target nucleic acid, so-called probes, are arranged on a solid support at a large number of sites. As a general method of manufacturing such probe arrays as described in EP No. 0373203B1, (1) the nucleic acid probe is synthesized on a solid support or (2) a previously synthesized probe is supplied onto a solid support. U.S. Pat. No. 5,405,783 discloses the method (1) in detail. Concerning the method (2), U.S. Pat. No. 5,601,980 and Science Vol. 270, p. 467 (1995) teach a method of arranging cDNA in an array by using a micropipet.

In the above method (1), it is not necessary to synthesize a nucleic acid probe in advance, since the nucleic acid probe is synthesized directly on a solid support. However, it is difficult to purify a probe nucleic acid synthesized on a solid support. The accuracy in determining the base sequence of a nucleic acid and in the detection of a target nucleic acid in a sample using a probe array largely depends on the correctness of the base sequence of the nucleic acid probe. For the method (1), therefore, further improvement in accuracy of a nucleic acid probe is required in order to manufacture a probe array of higher quality. In the method (2), a step of synthesizing a nucleic acid probe is required prior to the fixation of the nucleic acid probe on a solid support, but the nucleic acid probe can be purified before binding the probe to a solid support. For this reason, presently, the method (2) is considered to be more preferable than the method (1) as a method of manufacturing a probe array of high quality. However, the method (2) has a problem in the method of spotting a nucleic acid probe densely on a solid support. For example, when a probe array is used to determine the base sequence of a nucleic acid, it is preferable to arrange as many kinds of nucleic acid probes as possible on a solid support. When mutations in a gene are to be detected efficiently, it is preferable to arrange nucleic acid probes of sequences corresponding to the respective mutations on a solid support. In addition, when a target nucleic acid in a sample or to gene mutations and deletions are detected, it is desirable that the amount of the sample taken from a subject, specifically a blood sample, is a as small as possible. Thus, it is preferable that as much information as possible on the base sequence is obtained using a small sample amount. Considering these points, it is preferable that, for example, 10,000 or more nucleic acid probe spots per square inch are arranged in a probe array.

SUMMARY OF THE INVENTION

As the result of the research carried out by the inventors to solve above-discussed problems, they have found that an ink jet ejection method enables spotting of a probe in a markedly high density and achieved the present invention.

It is an object of the present invention to provide a method of spotting an extremely small amount of probe efficiently and accurately on a solid support without damaging the probe.

It is another object of the present invention to provide a probe array that can provide more information on nucleic acid more accurately even using a small amount of sample.

It is still another object of the present invention to provide a method of efficiently manufacturing a probe array, in which a large number of probes are bound to a solid support, with out damaging the probes.

It is further another object of the present invention to provide a method of efficiently detecting a target substance that may be contained in a sample.

It is still other object of the present invention to provide a method of identifying the structure of a target substance to obtain information on the structure of the target substance even from a small amount of sample.

According to one aspect of the present invention, there provided is a method of spotting a probe which can bind specifically to a target to a solid support. The method comprises a step of supplying a liquid containing a probe on a surface of a solid support by an ink jet method and adhering the liquid on the surface of the solid support. The use of the spotting method according to the above embodiment allows accurate and efficient provision of a probe on a solid support and efficient manufacturing of a probe array.

According to another aspect of the present invention, provided is a probe array comprised of a plurality of spots of a probe, where the spots are provided independently at a plurality of sites of the surface of a solid support in a density of 10,000 spots per square inch or higher. This probe array has spots in a remarkably high density so that much information can be obtained even from a small amount of sample.

According to further aspect of the present invention, provided is a method of manufacturing a probe array having a plurality of spots arranged independently in a plurality of sites on a surface of a solid support, the spots containing a probe which can bind specifically to a target substance comprising a step of supplying a liquid containing the probe and attaching the liquid to a predetermined site on the surface of the solid support by means of an ink jet method. According to this embodiment, a probe array comprising spots arranged in a high density can be efficiently manufactured without damaging the probe.

According to further aspect of the present invention, provided is a method of detecting a target substance by contacting a sample with each spot of a probe array having a probe that can bind specifically to a target substance that may be contained in a sample as a plurality of independent spots on a solid support to detect a reaction product of the target substance and the probe on the solid support to detect the presence/absence of the target substance in the sample wherein the respective spots are formed by spotting a liquid containing the probe on the solid support by the ink jet method. According to this embodiment, a target substance can be detected efficiently.

According to further aspect of the present invention, provided is a method of identifying a structure of a target substance contained in a sample comprising:

a step of preparing a probe array provided with spots of a probe, which can bind specifically to a specific substance, on a surface of a solid support;

a step of contacting the sample to the spots; and a step of detecting binding between the target substance and the probe.

U.S. Pat. No. 5,601,980 states that it is inappropriate to use a conventional ink jet method in spotting of a nucleic acid probe. In lines 31–52 in the second column of U.S. Pat. No. 5,601,980, it is said that the use of the ink jet printer technique in which a small amount of ink is ejected by pressure wave is inappropriate, because the pressure wave for ejecting ink may lead to a drastic rise in the ink temperature and damage the nucleic acid probe and scattering of the ink upon ejection may lead to contamination of adjacent probe spots. Considering this, U.S. Pat. No. 5,601,980 discloses a method of manufacturing a probe array in which a drop of a liquid containing a nucleic acid probe is formed on a tip of a micropipet utilizing gas pressure, while monitoring the size of the drop, application of pressure is terminated when the drop becomes the predetermined size, and the drop is applied on a solid support.

U.S. Pat. No. 5,474,796 discloses manufacturing of oligonucleotide array by forming a matrix of hydrophobic and hydrophilic parts on a solid support surface and ejecting four nucleotides sequentially to the hydrophilic part by means of a piezoelectric impulse jet pump apparatus and a method of determination of the base sequence of a target nucleic acid using the oligonucleotide array. However, these prior arts do not disclose a method in which nucleic acid probes each having a base sequence of a predetermined length is ejected in advance using an ink jet technique to arrange the nucleic acid probes accurately and densely.

DETAILED DESCRIPTION OF THE PREFERRED EMBODIMENTS (Outline of Method of Manufacturing Probe Array)

Figure 1:
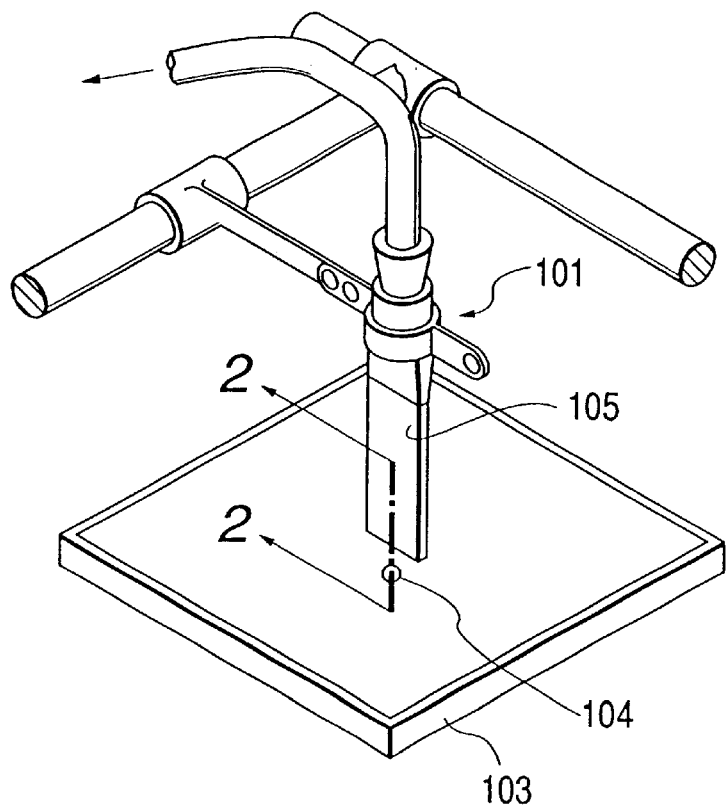
FIG. 1 is a schematic view illustrating a method of manufacturing a probe array using a bubble jet head.
Figure 2:
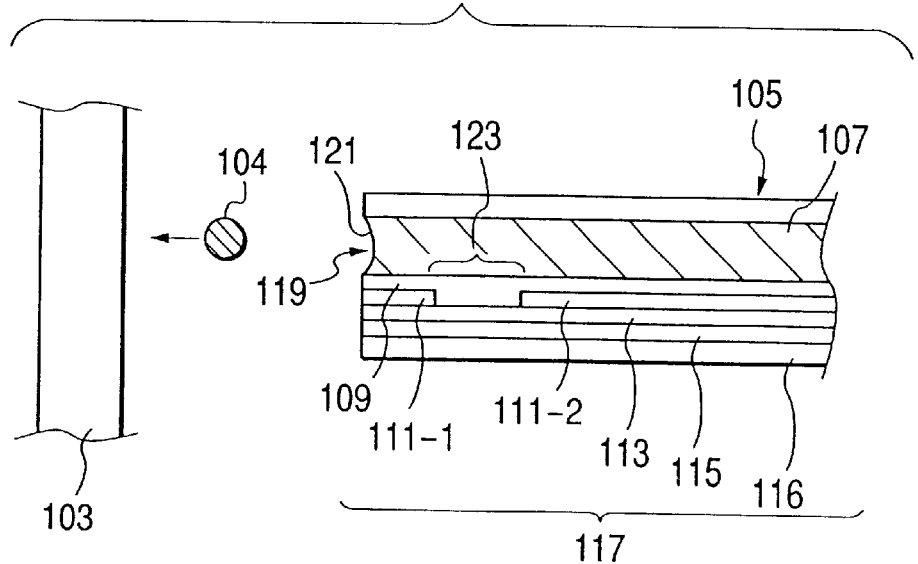
FIG. 2 is a cross sectional view taken along the line 2—2 of the bubble jet head of FIG. 1.

FIGS. 1 and 2 are schematic diagrams illustrating a method of manufacturing a probe array, for example, a nucleic acid probe array, according to one embodiment of the present invention. In FIG. 1, there are shown a liquid supply system (nozzle) 101 which ejectably retains a liquid containing a probe, for example, a nucleic acid probe, as an ejection liquid, a solid support 103 (for example, transparent glass plate, etc.) to which the nucleic acid probe is to be bound, and bubble jet head 105, a kind of ink jet heads, provided with a mechanism to apply heat energy to the liquid and thus eject the liquid. 104 denotes a liquid containing a nucleic acid probe ejected from the bubble jet head 105. FIG. 2 is a cross sectional view taken substantially along the line 2—2 of the bubble jet head 105 of FIG. 1. In FIG. 2, there are shown the bubble jet head 105, a liquid 107 containing a nucleic acid probe to be ejected, and a substrate part 117 with a heating member applying ejection energy to the liquid. The substrate part 117 comprises a protective film 109 made of silicone oxide etc., electrodes 111-1 and 111-2 made of aluminum etc., an exothermic resistance layer 113 made of nichrome etc., a heat accumulator layer 115, and a base material 116 made of alumina etc., with good heat radiating properties. A liquid 107 containing a nucleic acid probe comes up to an ejection orifice (ejection outlet) 119 and forms a meniscus 121 by the predetermined pressure. When electric signals from the electrodes 111-1 and 111-2 are supplied, a region shown by 123 (bubbling region) rapidly generates heat and a bubble appears in the liquid 107 contacting the region 123. The meniscus ejects at the pressure and the liquid 107 is ejected from the orifice 119 to fly toward the surface of a solid support 103. Although the ejectable amount of the liquid using a bubble jet head of such a structure depends on the size of the nozzle, etc., it can be controlled to be about 4–50 picoliters and is very useful as means to arrange nucleic acid probes in high density.

(Relation Between Ejected Liquid and Solid Support)

(Diameter of Spots on Solid Support)

In order to obtain the probe density as described above (for example, 10,000 probe spots per square inch, upper limit being about $1 \times 10^6$) on a solid support, it is preferable that the diameter of each spot is about 20–100 $\mu$m, for example, and that spots are independent each other. These spots are determined by properties of a liquid ejected from a bubble jet head and surface properties of the solid support to which the liquid is attached.

(Properties of Ejection Liquid)

Any liquid can be used as an ejection liquid, provided that the liquid can be ejected from a bubble jet head, the liquid ejected from the head arrives at the desired positions on a solid support, and the liquid does not damage the nucleic acid probe when it is mixed with nucleic acid probe and it is ejected.

From a viewpoint of liquid properties to be ejected from a bubble jet head, the liquid preferably has properties such as viscosity of 1–15 cps and surface tension of 30 dyn/cm or higher. When viscosity is 1–5 cps and surface tension is 30–50 dyn/cm, the position of arrival on a solid support becomes significantly accurate and it is especially suitable.

Then considering ink jet ejection properties of the liquid and stability of a nucleic acid probe in the liquid and, at ejection by a bubble jet, it is preferable to contain a nucleic acid probe of 2–5,000 mer, especially 2–60 mer in a concentration of 0.05–500 $\mu$M, especially 2–50 $\mu$M.

(Composition of Liquid)

Composition of a liquid to be ejected from a bubble jet head is not particularly restricted, provided that it does not substantially affect a nucleic acid probe when it is mixed with a nucleic acid probe or when it is ejected from the bubble jet head as described above, and a liquid composition normally ejectable to a solid support using the bubble jet head satisfies preferable conditions. However, a preferable liquid contains glycerin, urea, thiodiglycol or ethyleneglycol, isopropyl alcohol, and an acetylene alcohol shown by the following formula (I):

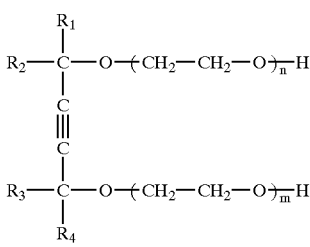

(I)

wherein R1, R2, R3 and R4 represent alkyl, groups, specifically straight or branched alkyl groups containing 1–4 carbons, m and n represent integers, and m=0 and n=0 or $1 \leq m+n \leq 30$, and when m+n=1, m or n is zero.

More specifically, a liquid comprising 5–10 wt % of urea, 5–10 wt % of glycerin, 5–10 wt % of thiodiglycol, and 0.02–5 wt %, more preferably 0.5–1 wt % of an acetylene alcohol shown by the above formula (I) is preferably used.

When this liquid is used, spots obtained by ejecting the liquid containing a nucleic acid probe from a bubble jet head and attached on a solid support are round, and an area where the ejected liquid is attached is restricted. Thus, even when a nucleic acid probe is spotted densely, connection of the adjacent spots can be effectively prevented. No degradation of the nucleic acid probe spotted on a solid support is observed. However, the properties of the liquid used in manufacturing a nucleic acid probe array according to the present invention are not restricted to those mentioned above. For example, when structures like wells are provided on a solid support surface to prevent spreading of the liquid applied on the solid support by a bubble jet head and mixing with adjacent spots, a liquid of a viscosity and surface tension out of the above range, and a nucleic acid probe of a base length and concentration out of the above range can be used.

(Kinds of Functional Groups of Solid Support and Nucleic Acids)

A method to securely bind the nucleic acid probe to the solid support, as well as to effectively retain the applied spot of a nucleic acid probe at a more defined position on the solid support to prevent cross contamination between adjacent spots, one can endow the probe and the solid support with functional groups which can react each other.

(SH Group and Maleimido Group)

The combination use of the maleimido group and the thiol (—SH) group can be mentioned as a preferable example. That is, by binding a thiol (—SH) group to the terminus of a nucleic acid probe and treating the solid support surface to have a maleimido group, the thiol group in a nucleic acid probe when supplied to the surface of the solid support reacts with the maleimido group of the solid support to immobilize the nucleic acid probe on the support, forming probe spots on the predetermined positions on the solid support. Especially, when such a nucleic acid probe containing a thiol group at the terminus is dissolved in a liquid of the above-mentioned composition, and applied on a solid support surface having maleimido groups by means of a bubble jet head, the nucleic acid probe solution can form a very small spot on the solid support. As a result, small spots of a nucleic acid probe can be formed on the predetermined positions of the surface of the solid support. In this case, it is not necessary to provide a construction such as wells comprised of partly hydrophilic and hydrophobic matrix on the surface of the solid support to prevent connection between spots.

For example, when a liquid containing a nucleic acid probe of 18 mer nucleotides at a concentration of 8 $\mu$M and controlled to have the viscosity and surface tension within the above ranges was ejected from a nozzle (an amount of ejection about 24 picoliters) using a bubble jet printer (Product name: BJC620; Canon Inc., modified to print on a flat plane) with a space between the solid support and the nozzle tip of the bubble jet head set about 1.2–1.5 mm, spots of a diameter about 70–100 $\mu$m could be formed and no spots due to scattering when the ejected liquid hit the surface of the solid support (referred to as satellite spots hereinafter) were observed. Reaction between maleimido groups on the solid support and SH groups at the terminus of the nucleic acid probes is completed in about 30 minutes at room temperature (25° C.), although depending on the conditions of an ejected liquid. The time required is shorter than that required when a piezoelectric jet head is used to eject a liquid. Although the reason is not known, it is considered that the temperature of the nucleic acid probe solution in the bubble jet head is elevated according to its base principle so that the efficiency of reaction between a maleimido group and a thiol group is increased to shorten the reaction time.

Incidentally, a thiol group tends to become unstable under an alkaline or neutral conditions and a disulfide bond (—S—S—), which gives a dimer, may be formed. In order to prevent the disulfide bond formation and to accomplish an effective reaction between a thiol group and a maleimido group, it is preferable to add thiodiglycol to the ejection liquid.

In order to introduce maleimido group onto a solid support surface, various methods can be employed. For example, when a glass substrate is used as the solid support, maleimido group can be incorporated onto the surface of the solid support by an introduction of amino group onto the substrate and the following reaction between the amino group and a reagent containing N-(6-maleimidocaproyloxy) succinimide (EMCS reagent: Dojin Co., Ltd.). The amino group introduction onto the surface can be conducted by reacting an aminosilane coupling agent with the glass substrate.

(Structural Formula of EMCS)

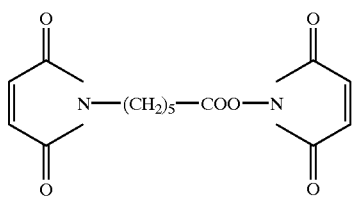

A nucleic acid probe having a thiol, group at the terminus thereof can be obtained by synthesizing a nucleic acid using 5'-thiol-modifier C6 (Glen Research Co., Ltd.) as a reagent for the 5'-terminus on an automatic DNA synthesizer followed by usual deprotection reaction and purification by high performance liquid chromatography.

(Amino Group and Epoxy Group)

As functional groups used for immobilization other than the above-mentioned combination of the thiol group and the maleimido group, a combination of the epoxy group (on solid support) and the amino group (nucleic acid probe terminus) may also be used. Epoxy groups can be introduced onto a solid support surface, for example, by applying polyglycidyl methacrylate having an epoxy group onto the surface of a solid support of a resin, or by applying a silane coupling agent having an epoxy group onto the surface of glass solid support for reaction.

As explained above, when functional groups are introduced into a solid support surface and a terminus of a ss-nucleic acid probe to form covalent bonds, the nucleic acid probe is more firmly fixed to the solid support. In addition, since the nucleic acid probe always binds to the solid support at its terminus, the states of the nucleic acid probe in each spot become homogeneous. As a result, hybridization between the nucleic acid probes and target nucleic acids occurs in uniform conditions, thus the detection of a target nucleic acid and the identification of a base sequence with further improved accuracy can be realized. When nucleic acid probes having a functional group on each terminus are covalently bound to a solid support, a probe array can be produced quantitatively without differences in the amount of bound probe DNA due to difference in sequence or length, compared with nucleic acid probes fixed on a solid support by non-covalent bond (for example, electrostatically, etc.). In addition, all parts of the nucleic acid participate in hybridization reaction, efficiency of hybridization can be markedly improved. In addition, a linker such as alkylene groups of 1–7 carbons or ethylene glycol derivatives can be present between the ss nucleic acid portion which hybridizes with a target nucleic acid and the functional group for binding with a solid support. When such a nucleic acid probe is bound to a solid support, a predetermined space can be provided between the surface of the solid support and the nucleic acid probe so that efficacy of reaction between a nucleic acid probe and a target nucleic acid can be expected to be improved further.

(Manufacturing Method of Probe)

One of the preferred embodiments of the probe array-manufacturing method will now be explained. First, a liquid containing 7.5 wt % of glycerin, 7.5 wt % of urea, 7.5% of thiodiglycol, and 1 wt % of an acetylene alcohol shown by the above general formula (I) (for example, Product Name: Acetylenol EH; Kawaken Fine Chemical Co., Ltd.) is prepared. A ss nucleic acid probe of a length of, for example, about 2–5,000 mer, especially, about 2–60 mer, having a thiol group at the terminus is synthesized using an automatic DNA synthesizer. Nest, the nucleic acid probe is mixed in the above liquid at a concentration in a range of 0.05–500 $\mu$M, especially 2–50 $\mu$M, to produce a liquid to be ejected having a viscosity of 1–15 cps, especially 1–5 cps, and surface tension of 30 dyn/cm or higher, especially 30–50 dyn/cm. Then, this ejection liquid is filled in a nozzle of a bubble jet head, for example. Maleimido groups are introduced on a solid support surface according to the above method. The solid support is placed so that a distance between the surface of the solid support having maleimido groups and the nozzle tip of the bubble jet head becomes as close as about 1.2–1.5 mm, and the bubble jet head is driven to eject the liquid. Here, as the ejection conditions, it is desirable to set printing pattern so as not to allow the connection between the spots on a solid support each other. When a bubble jet head of which resolution is 360×720 dpi is used, for spotting, preferable conditions are that one liquid ejection is followed by twice idle ejections in the 360 dpi direction and one liquid ejection is followed by 5 times idle ejections in the 720 dpi direction. These conditions can provide a space of about 100 $\mu$m between spots and sufficiently prevent contamination between adjacent spots. Then, the solid support is stood, for example, in a humid chamber, until a reaction between the maleimido groups on a solid support and the thiol groups of nucleic acid probes in a liquid proceeds and the nucleic acid probes are securely fixed on the solid support. It is sufficient to leave it at room temperature (about 25° C.) for about 30 minutes as described above. Then, the nucleic acid probes not reacted on the solid support are washed a way to obtain a nucleic acid probe array.

Now, in order to improve detection accuracy (S/N ratio) in, for example, detection of a target nucleic acid using this nucleic acid probe array, it is preferable to block the solid support surface after the nucleic acid probes were fixed to the support to prevent the surface areas not binding the nucleic acid probes from reacting with a target nucleic acid, etc., contained in a sample. Blocking can be performed by, for example, immersing the solid support in a 2% aqueous bovine serum albumin solution for two hours or decomposing maleimido groups not bound to the nucleic acid probes on the surface of the solid support. For example, DTT (dithiothreitol), $\beta$-mercaptoethanol, etc. can be used. However, in terms of an effect of preventing adsorption of target DNA, an aqueous solution of bovine serum albumin is the most suitable. This step of blocking may be performed, as required. For example, this blocking step can be omitted, when a sample can be supplied restrictively to the respective spots of the probe array and any sample would not attach substantially to the parts other than the probe spots. The blocking step can be omitted, also when wells have been formed on the solid support beforehand, and parts other than wells are processed to inhibit attachment of nucleic acid probes.

The probe arrays manufactured by such a method may have a plurality of spots containing the same nucleic acid probe or a plurality of spots each containing a different nucleic acid probe, depending on applications. The probe array in which the nucleic acid probes are arranged at a high density prepared a mentioned above, can then be used for the detection of a target ss nucleic acid and the identification of a base sequence. For example, when a target ss nucleic acid of a known base sequence which may be present in a test sample is detected, a ss nucleic acid having a base sequence complementary to that of the target nucleic acid is used as the probe, and the probe array in which a plurality of spots containing the probe are arranged on a solid support is prepared. Each sample is supplied to each spot of the probe array, and the probe array is left standing under conditions allowing hybridization between the target nucleic acid and the probe, then the presence/absence of hybrid in each spot is detected by a known method such as fluorescent detection. This enables detection of the presence/absence of the target substance in a sample. When a probe array is used to identify a base sequence of a target ss nucleic acid contained in a sample, a plurality of ss nucleic acids having base sequences complementary to the presumed sequences of the target nucleic acid are spotted as probes on the solid support. Then, aliquots of the sample are supplied to the respective spots and incubated under conditions allowing hybridization of the target nucleic acid and the probe, and then the presence/absence of hybridization at each spot is detected by a known method such as the fluorescence method. This enables identification of a base sequence of a target ss nucleic acid. As other applications of the probe array according to the present invention, for example, application to screening of specific base sequences recognized by DNA binding protein and chemical substances having a property to bind to DNA can be considered.

(Kinds of Ink Jet Head)

Although a constitution in which a nucleic acid probe is applied to a solid support by means of a bubble jet head is solely illustrated above, a piezoelectric jet head ejecting a liquid in a nozzle by vibration pressure of piezoelectric elements can also be used in the present invention. However, a bubble jet head is suitably used in the present invention, since a binding reaction to a solid support is completed in a short period of time and secondary structure of DNA is unfolded by heat so that efficiency of the subsequent hybridization reaction can be increased, as described above.

In addition, an ink jet system having a plurality of heads can be used to form a plurality of spots simultaneously on a solid support so that two or more spots may contain different nucleic acid probes.

(PNA/DNA)

The present invention has been illustrated using a nucleic acid probe as an example of probes. Nucleic acid probes include deoxyribonucleic acid (DNA) probes, ribonucleic acid (RNA) probes, and peptide nucleic acid (PNA) probes. PNAs are synthetic oligonucleotides in which four bases (adenine, guanine, thymine, and cytosine) contained in DNA are bound to a peptide backbone, not to a sugar-phosphate backbone as shown in the following formula (II):

PNA Structural Formula (II)

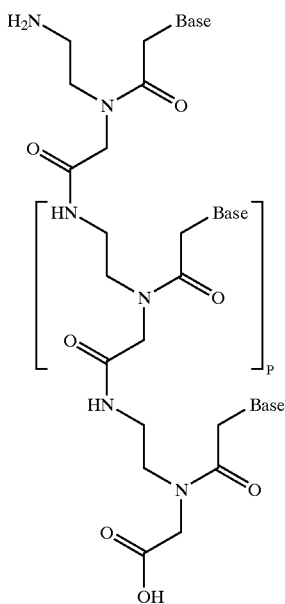

wherein "Base" represents any one of four bases (adenine, guanine, thymine, and cytosine) contained in DNA, and p represents a base length of the PNA. PNAs can be synthesized, for example, by methods known as tBOC-type solid phase synthesis and Fmoc-type solid phase synthesis. PNAs are more resistant to enzymes such as nucleases and proteases as compared to natural oligonucleotides of DNA and RNA, hardly or not cleaved enzymatically, and stable in the serum. Due to the absence of the sugar moiety or phosphate groups, PNAs are rarely affected by ionic strength of a buffer. Therefore, it is not required to control a salt concentration, etc., when PNAs are reacted with a target ss nucleic acid. In addition, due to the absence of electrostatic repulsion, a hybrid between PNA and a target ss nucleic acid is considered to be more heat-stable than those between a DNA probe and a target ss nucleic acid and between an RNA probe and a target ss nucleic acid. From these characteristics, PNAs are expected as probes used for the detection of a target nucleic acid and the determination of a base sequence. The method of manufacturing a nucleic acid probe array according to the present invention is effective also when a PNA probe is used as a nucleic acid probe and can easily manufacture a PNA probe array in which PNA probes are arranged densely and very accurately. Specifically, for example to increase the density of a probe array by securing a PNA probe on restricted positions on a solid support, as in the case of DNA probes and RNA probes, two kinds of functional groups which can react each other into the terminus of a PNA probe and a solid support surface are introduced respectively. A preferred combination of reactive groups is, as mentioned above, a combination of a thiol group (at the terminus of PNA) and a maleimido group (a solid support surface). A thiol group can be introduced at the terminus of PNA by, for example, introducing a cysteine ($CH(NH_2)(COOH)CH_2SH$) group, etc., containing a thiol group in the N-terminus (corresponding to the 5-terminus of DNA) of a PNA probe. A cysteine group can be introduced at the N-terminus of a PNA probe by, for example, reacting the amino group of the N-terminus of a PNA probe and the carboxyl group of cysteine. Further, using a suitable linker such as those containing an amino group and a carboxyl group such as $N_2H(CH_2)_2O(CH_2)_2OCH_2COOH$, the amino group at N-terminus of a PNA probe is reacted with the carboxyl group of the linker and then the amino group of the linker is reacted with the carboxyl group of cysteine so as to bind cysteine to the PNA probe via the linker. When a binding group to a solid support is introduced via a linker as mentioned above, a part of PNA probe interactive with a target substance can be separated from the solid support by a predetermined distance so that a further improvement in hybridization efficiency is expected.

PNA may have lower water-solubility than DNA of the same base length as the polymer length of the PNA. Thus, when a liquid for ink jet ejection is prepared, it is preferable to dissolve PNA in trifluoroacetic acid (for example, a 0.1 wt % aqueous solution of trifluoroacetic acid) etc., in advance and then prepare an ejection liquid of properties compatible to ink jet ejection using various solvents mentioned above. In particular, prior dissolution in trifluoroacetic acid can prevent the conversion of the terminal cysteine residues to cystine due to the oxidation of thiol groups of PNA. Thus it is preferable for further improvement in efficiency of a reaction between the thiol group of PNA and the maleimido group on a solid support surface. Although the reaction time of 30 min is sufficient for a reaction between a thiol group introduced at the terminus of a DNA probe or an RNA probe and a maleimido group on a solid support surface (when a bubble jet head is used), it is preferable to proceed a reaction for about 2 hours in case of PNA even using a bubble jet head.

In the present invention, probes are not limited to nucleic acid probes, and include substances which can bind specifically to a target substance in a sample to be detected or analyzed, for example, ligands which can bind specifically to receptors, receptors which can bind specifically to ligands, oligopeptides and polypeptides which can bind to oligopeptides and polypeptides having specific amino acid sequences, and proteins (for example, antibodies, antigens, enzymes, etc.).

As mentioned above, according to the method of manufacturing a probe array comprising a step of supplying a probe solution to a solid support using an ink jet ejection process, a probe array can be manufactured very easily. In particular, when functional groups are introduced both in a nucleic acid probe and in a solid support surface so as to form a covalent bond between them, adjacent spots do not connect each other even when a solid support on which wells, etc. have not been provided in advance, that is, a solid support which is substantially flat and has homogenous surface properties (water-wettability, etc.) is used. As a result, a nucleic acid probe array in which spots of a nucleic acid probe are arranged accurately and densely can be manufactured extremely efficiently and at a low cost.

This description does not intend to exclude a solid support provided with wells on the surface in the present invention. For example, when opaque matrix pattern (referred to as a black (BM) matrix hereinafter) is previously formed between wells to which a probe solution is supplied, detection accuracy (SN ratio) can be further improved in optical detection (for example, detection of fluorescence) of hybridization between a probe and a target substance. In addition, when a matrix whose surface has a low affinity to a probe solution is provided between adjacent wells, the probe solution can be smoothly supplied to desired wells, even when the solution is supplied to somewhat offset positions during supply of the probe solution to wells. To enjoy such an effect, it can be used a solid support on the surface of which wells are provided. A solid support with a matrix formed on its surface, a manufacturing method thereof, and a method of using the solid support according to this embodiment are described below.

Figure 5A:
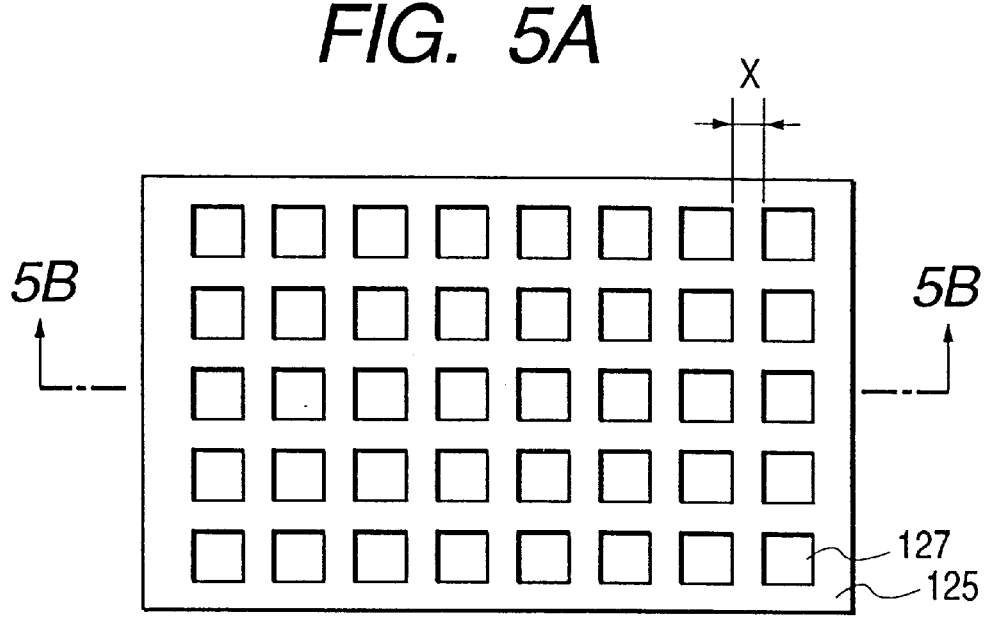
FIG. 5A is a schematic plan view of one embodiment of a probe array of the present invention.
Figure 5B:
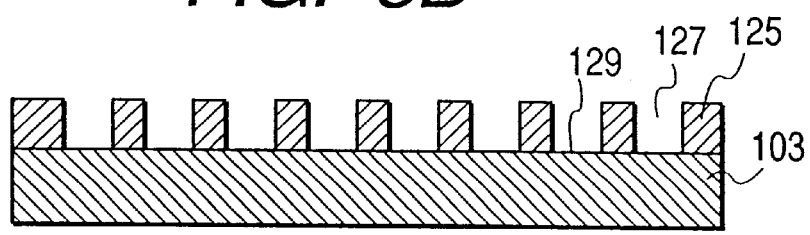
FIG. 5B is a cross sectional view taken along the line 5B—5B in FIG. 5A.

FIGS. 5A and 5B show examples of a probe array according to this embodiment of the present invention. FIG. 5A is a plan view and FIG. 5B is a cross sectional view taken along the line 5B—5B of FIG. 5A. This probe array has a configuration in which a matrix pattern 125 in a framework structure containing hollowed parts (wells) 127 are arranged in a form of a matrix are formed on a solid support 103. The wells 127 separated by the matrix pattern 125 (projecting part) are provided as through holes (bored parts) in the matrix pattern, the side walls of the holes being formed by projecting parts, and a surface of the solid support 103 is exposed at the bottom 129. The exposed surface of the solid support 103 forms a surface which can bind to a probe, and probes (not shown) are fixed to the predetermined wells.

Materials to form the matrix pattern are preferably those which make the matrix pattern opaque, considering improvement in detection sensitivity, S/N ratio, and reliability, when a reaction product of a probe and a target substance is detected optically, for example, by measuring florescence emitted from the reaction product. As these materials, metals (chromium, aluminum, gold, etc.) and black resins, etc., can be exemplified. As the black resins, included are resins such as acrylic, polycarbonate, polystyrene, polyethylene, polyimide, acrylic monomer, and urethane acrylate and photosensitive resins such as photoresists containing black dyes or pigments. As specific examples of photosensitive resins, for example, UV resist, DEEP-UV resist, ultraviolet cure resins can be used. As UV resists, negative resists such as cyclized polyisoprene-aromatic bisazide resists, and phenol resin-aromatic azide compound resists, and positive resists such as novolak resin-diazonaphtoquinone resists can be mentioned. As DEEP-UV resists, positive resists, for example, radiolytic polymer resists such as polymethyl methacrylate, polymethylene sulfone, polyhexafluorobutyl methacrylate, polymethylisopropenyl ketone, and poly-1-trimethylsilyl propylene bromide and dissolution suppressant resists such as o-nitrobenzyl ester cholate, and negative resists such as polyvinylphenol-3,3'-diazidediphenyl sulfone and glycidyl polymethacrylate can be mentioned.

As ultraviolet curing resins, polyester acrylate, epoxy acrylate and urethane acrylate, etc., containing about 2–10 wt % of one or more photopolymerization initiators selected from a group consisting of benzophenone and its substituted derivatives, benzoin and its substituted derivatives, acetophenone and its substituted derivatives, and oxime compounds such benzyl, etc can be mentioned.

As black pigments, carbon black and black organic pigments can be used.

When the reaction product of a probe and a target substance is not detected optically and when light from a matrix does not affect optical detection of a reaction product, the use of non-light-shielding substances as a material for a matrix pattern is not excluded.

As one of the methods of forming a matrix pattern using the above materials, a method in which a photoresist layer is formed on a resin or a metal layer formed on the surface of a substrate, and after the patterning of the resist layer, the resin is patterned by a process such as etching. When a photosensitive resin is used, the resin itself can be exposed, developed, and cured if required, by a process of photolithography using a photomask for patterning. When a matrix 125 is made of a resin, the surface of the matrix 125 is hydrophobic. This configuration is preferable when an aqueous solution is used as a solution containing a probe and supplied to wells. That is, when a probe solution is supplied to wells by the ink jet method, the probe solution can be supplied very smoothly to desired wells, even when the probe solution is supplied in slightly offset positions. In addition, when different probes are supplied to adjacent wells simultaneously, cross-contamination of these different probe solutions supplied to the wells can be prevented.

Since a solution of a probe, a biomaterial, such as peptides and nucleic acids, is often an aqueous solution, this constitution in which a matrix pattern is water-repellent can be suitably used in such occasions.

Next, a method of making a bottom of a well (an exposed part of a solid support surface) which can bind a probe is described. A functional group to be retained on the bottom of a well is determined by the functional group to be carried on a probe. For example, when a nucleic acid probe in which a thiol group is introduced at the terminus is used, previous introduction of a maleimido group to a solid support surface, as mentioned above, makes the thiol group of the nucleic acid probe supplied to wells form a covalent bond with the maleimido group on the surface of the solid support and the nucleic acid probe is then fixed on the surface of the solid support. Similarly, with a nucleic acid probe having an amino group at the terminus, it is preferable to introduce epoxy groups to a solid support surface. As other combinations of these functional groups, for example, a combination of a carboxyl group for a nucleic acid probe (by introducing a succinimide derivative to the terminus of a nucleic acid probe) and an amino group for a solid support surface is preferable. This combination of amino and epoxy groups is inferior in immobilization of the ink jet-ejected nucleic acid probe on a solid support to a combination of thiol and maleimido groups but to a negligible extent when wells are provided on the solid support.

The amino or epoxy group can be introduced to a glass plate as the solid support by, first treating the surface of the glass plate with an alkali solution such as potassium hydroxide and sodium hydroxide to expose hydroxyl groups (silanol groups) to the surface, and then reacting a silane coupling agent containing a silane compound to which an amino group has been introduced (for example, N-$\beta$-(aminoethyl)-$\gamma$-aminopropyltrimethoxysilane, etc.) or a silane compound to which an epoxy group has been introduced (for example, $\gamma$-glycidoxypropyltrimethoxysilane, etc.) with a hydroxyl group of the surface of the glass plate. To introduce maleimido groups to the surface of the glass plate, the amino groups introduced by the above method are reacted with N-maleimidocaproyloxy succinimide or succinimidyl-4-(maleimido phenyl)butyrate, etc.

The structures of N-β-(aminoethyl)-γ-aminopropyltrimethoxysilane, γ-glycidoxypropyltrimethoxysilane, and succinimidyl-4-(maleimido phenyl)butyrate are shown below:

N-β-(aminoethyl)-γ-aminopropyltrimethoxysilane
$(CH_3O)_2SiC_3H_6NHC_2H_4NH_2$

γ-glycidoxypropyltrimethoxysilane

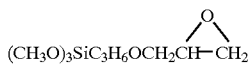

Succinimidyl-4-(maleimido phenyl)butyrate

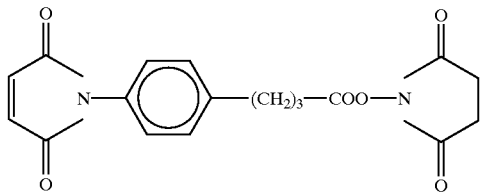

When an epoxy group is introduced to a solid support surface in the above surface treatment of a solid support, the base of wells can be made hydrophilic after binding the epoxy groups to a probe, by opening unreacted epoxy rings using an aqueous solution of ethanol amine, etc., to change them into hydroxyl groups. This operation is preferable, when an aqueous solvent containing a target substance that will react specifically to a probe is supplied to wells to which the probe has been bound.

When a resin plate is used as a solid support, hydroxyl groups, carboxyl groups, or amino groups can be introduced to the surface of resin substrate according to the method described in Chapter 5 of "Organic Thin Films and Surface", Vol. 20, Academic Press. Alternatively, after introducing hydroxyl groups by this method, as is shown for the glass plate mentioned above, amino groups or epoxy groups can be introduced by using a silane compound having amino group or epoxy group. Further a maleimido group can be introduced. Functional groups can be introduced either before or after the matrix pattern is formed on a solid support. Before matrix pattern formation, a reaction solution required for introduction of a functional group can be supplied to a solid support surface by spin coating or dip coating, etc. After matrix formation, a reaction solution can be supplied to each well by the ink jet method, etc.

To bind a probe to a resin substrate, for example, hydroxyl groups are introduced by oxidation of the surface of a resin substrate, then the hydroxyl groups are reacted with a silane coupling agent comprised of a silane compound containing an amino group to introduce amino groups, and each amino group is reacted with a functional group of a probe, as described in Japanese Patent Application Laid-Open No. 60-015560.

When the substrate after treatment is hydrophilic, above-mentioned resins to make matrix pattern formation can be used without any treatment as a relatively water-repellent material. When further repellency is required, a water-repellant can be added to a matrix material. When a matrix pattern is formed from a photosensitive resin such as photoresists, post-baking under appropriate conditions following exposure and development can provide stronger repellency to the matrix pattern.

When a probe solution is lipophilic, although it has been explained mainly on a hydrophillic probe solution, treatment can be performed in opposite.

The size and shape of wells in a matrix pattern can be selected according to the size of a substrate, the size of an array as a whole finally prepared, the number and a type of probe constituting the array, or a method of forming a matrix pattern, a method of supplying a probe solution to wells in matrix pattern, and a method of detection, etc.

Cross section of wells by a plane parallel to the substrate can be various shapes, in addition to squares as shown in FIG. 5, such as rectangles, various polygons, circles, and ovals.

Preferably, wells have a maximum width of 300 μm or less, considering the number of reactants and a size of a whole array. For example, as shown in FIG. 5, when a cross section taken parallel to a substrate is square, one side can be 200 μm or less in length. Preferably, when wells are rectangular, the maximum side is 200 μm or less, and when wells are round, the diameter is 200 μm or less. The minimum limit in length is about 1 μm.

Wells can be arranged in various patterns as required. Wells can be arranged at equal intervals making rows and columns as shown in FIG. 5, or wells can be arranged so as to shift from the positions of wells in adjacent lines.

A distance between adjacent wells is preferably set not to cause cross-contamination even when the ejection positions are somewhat offset from the position of the target well to which a probe solution is supplied by, for example, the ink jet method. In addition, considering a size of a whole array, cross-contamination, and handling properties in supply of various solutions, the distance between the adjacent wells is in the range of ½ to 2 times the maximum width.

For example, it is desirable 100×100 or 1,000×1,000 or more types of probes are present in a probe array for fully displaying functions of combinatorial chemistry, and the size of a substrate is desirably 1 inch×1 inch or 1 cm×1 cm, to be suitable for automation of operations such as probe fixation, sample supply and detection, thus for square wells it is preferable to set a side of a square of a well at 1–200 μm or less and a distance between adjacent wells is at 200 μm or less, considering the matrix size.

The thickness of a matrix (height from the solid support surface) is determined considering a method of forming the matrix pattern, volume of wells, and volume of a probe solution supplied. It is preferably 1–20 μm. Such a thickness enables, when a probe solution is supplied to each well by the ink jet ejection method, to retain the probe solution at predetermined positions on a solid support and to prevent cross-contamination very efficiently, even when the properties of the probe solution should be not suitable for forming small spots on the solid support surface, in relation to the conditions for the ink jet ejection method.

When a well has a size of the upper limits of the above-described desirable ranges, that is, 200 μm×200 μm×20 μm, the well volume is 800 pl. When this size is used and a distance between adjacent wells (x in FIG. 1) is also set at 200 μm, a density of wells of 625 wells/cm² is obtained. That is, an array with a well density of an order of $10^2$ wells/cm² or more can be obtained. When a well is a square with a side of 5 μm, a distance between adjacent wells is set at 5 μm, and a thickness of the matrix pattern is set at 4 μm, a volume of a well is 0.1 pl and the density of wells is 1000000 wells/cm². Since patterning of 5 μm×5 μm×4 μm is possible in the present fine processing technology, an array with a well density of an order of $10^6$ wells/cm² or more can be included in the scope of the present invention.

In this embodiment, the feeding volume of a probe solution or a substance to be reacted with a probe supplied to a well is 0.1 picoliters (pl) to 1 nanoliter (nl) from the above calculation, when the volume to be supplied is deemed to be the same as or almost the same as the volume of the well. When a matrix has little affinity to a solution to be supplied, it is possible to supply the solution in an volume exceeding the well volume which is retained above the opening of the well due to surface tension, depending to the type of the solution. In such a case, for example, a solution in a volume 10 to several tens of times larger than that of the well can be supplied and retained. That is, several picoliters to several tens of nanoliters of a solution are supplied. In any cases, a probe solution is preferably supplied to wells using the ink jet method that can supply such a small amount of solution with position accuracy and supply accuracy, although microdispensers and micropipettes can also be used. In the ink jet printing, an ink is ejected with positioning at high accuracy of an order of $\mu$m. This method is thus quite suitable for supplying a solution to wells. Since a volume of ink to be ejected is several tens of picoliters to several nanoliters, the ink jet method can be said to be suitable for supplying a solution, also in this respect.

According to this embodiment, spreading of droplets can be controlled quantitatively by the reaction between a nucleic acid probe and a solid support surface as well as by wells. In addition, even when a liquid is ejected in a somewhat offset direction, when a droplet lands on an area containing a well, the droplet part on the matrix is repelled and drawn into the well smoothly, since the matrix has no affinity to the ejected solution.

The ink jet method used in the present invention is not particularly restricted, and a piezo jet method, a bubble jet method utilizing thermal bubbling, etc., can be employed.

Any materials can be used as the solid support 103 according to one embodiment of the present invention, so long as various functional groups as described above can be introduced to the surface. According to the second embodiment of the present invention, preferred materials are those on the surface of which a matrix pattern can be formed. When the reaction product of a probe and a target substance is detected optically by a detection system via a solid support, the solid support is preferably transparent. As these materials, glass including synthetic quartz and fused quartz, silicone, acrylic resins, polycarbonate resins, polystyrene resins, and vinyl chloride resins, etc. can be mentioned. When the reaction product is detected optically not via a solid support, it is preferable to use an optically black solid support, and resin substrates containing black dyes or pigments such as carbon black are used.

In the present invention, a solution which may contain a substance which reacts with the probe (a test solution) is supplied to a probe array and left under suitable reaction conditions to proceed the reaction. When plural test solutions must be supplied to the array, at least one test solution is supplied to plural wells in the probe array, respectively. In this case, as shown above, when the supplied solution has an affinity to wells containing a fixed probe in the already formed probe array and has no affinity to a matrix pattern, quantitative supply of the solution to a restricted supply area can be achieved without cross-contamination. Since most of biomaterials are water-soluble, wells are hydrophilic and a matrix pattern is water-repellent. In addition, the use of the ink jet method in supply of these substances for reaction as shown above can quantitatively supply a very small amount of solution.

According to the present invention, very small amounts of a probe solution and a test solution are used. Thus, it is desirable to include conditions for preventing evaporation or vaporization of the supplied solutions for both cases.

The present invention is described in more detail referring to the following examples.

EXAMPLE 1

Manufacturing of Nucleic Acid Probe Array Using Bubble Jet Printer and Evaluation of the Probe Array (1) Washing of Substrate A glass plate of 1 inch×1 inch was placed in a rack and immersed in an ultrasonic washing detergent overnight. After ultrasonic washing in the detergent for 20 minutes, the detergent was removed by rinsing with water. After rinsing with distilled water, ultrasonic treatment was performed in a container containing distilled water for 20 minutes. The glass plate was immersed for 10 minutes in a 1 N sodium hydroxide solution preheated to 80° C. Then, the plate was washed with water and distilled water to prepare a glass plate for a probe array.

(2) Surface Treatment

A 1 wt % aqueous solution of a silane coupling agent (Product name: KBM603; Shin-Etsu Chemical Co., Ltd.) containing a silane compound having an amino group (N-$\beta$-(aminoethyl)-$\gamma$-aminopropyltrimethoxysilane) was stirred at room temperature for 2 hours to hydrolyze methoxy groups of the above silane compound. Then, the substrate was immersed in this solution at room temperature (25° C.) for 20 minutes, drawn up from the solution, and dried by blowing nitrogen gas to both sides of the glass plate. Then, the glass plate was baked for 1 hour in an oven heated to 120° C. to complete silane coupling treatment to introduce an amino group on the surface of the substrate. Then, 2.7 mg of N-(6-maleimidocaproyloxy) succinimide (Dojin Co., Ltd.) (abbreviated as EMCS hereinafter) was weighed and dissolved in a mixture of DMSO/ethanol (1:1) to a final concentration of 0.3 mg/ml to prepare an EMCS solution. The glass plate subjected to silane coupling treatment was immersed in the EMCS solution at room temperature for 2 hours for the reaction of the amino groups carried on the surface of the glass plate by silane coupling treatment and the carboxyl groups of the EMCS solution. In this condition, the glass plate obtained maleimido groups derived from EMCS on its surface. The glass plate drawn up from the EMCS solution was washed successively with a mixed solvent of dimethylsulfoxide and ethanol and with ethanol and then dried under a nitrogen gas atmosphere.

(3) Synthesis of DNA Probe

A single-stranded (ss) nucleic acid of SEQ ID No. 1 was synthesized using an automatic DNA synthesizer. A thiol (—SH) group was introduced at the terminus of the ss DNA of SEQ ID No. 1 using Thiol-Modifier (Glen Research Co., Ltd.) during synthesis by the automatic DNA synthesizer. Following ordinary deprotection, DNA was recovered, purified with high performance liquid chromatography, and used in the following experiments.

SEQ ID No. 1

$5'$HS—(CH$_2$)$_6$—O—PO$_2$O—ACTGGCCGTCGTTTTACA $3'$ (4) DNA Ejection and Binding to Substrate Using BJ Printer The ssDNA of SEQ ID No. 1 was dissolved in a TE solution (10 mM Tris-HCl (pH 8)/1 mM EDTA aqueous solution) to a final concentration of about 400 mg/ml to prepare a ssDNA solution (accurate concentration is calculated from absorbance).

An aqueous solution containing glycerin at 7.5 wt %, urea at 7.5 wt %, thiodiglycol at 7.5 wt %, and an acetylene alcohol (Product name: Acetylenol EH; Kawaken Fine Chemical Co., Ltd.) having the above general formula (I) at 1 wt % was prepared and added to the DNA solution to adjust a final concentration of the ssDNA to 8 µM. This liquid had surface tension in a range of 30–50 dyn/cm and viscosity of 1.8 cps (E-type viscometer: Tokyo Keiki Co., Ltd.). This liquid was filled in an ink tank of a bubble jet printer (Product name: BJC620; Canon Inc.) and the ink tank was mounted on a bubble jet head. The bubble jet printer used here (Product name: BJC620; Canon Inc.) had been modified to enable printing on a plate. This bubble jet printer can print with a resolution of 360×720 dpi. The glass plate treated in the above (2) was then mounted on this printer and the liquid containing the probe nucleic acid was spotted on the glass plate. The distance between the nozzle tip of the bubble jet head and the surface of the glass plate was 1.2–1.5 mm. The conditions for spotting were set in such a manner that the liquid was spotted once followed by 2 idle ejections in a direction of 360 dpi and then spotted once followed by 5 idle ejections in a direction of 720 dpi. After completion of spotting, the glass plate was left to stand in a humid chamber for 30 minutes to complete the reaction between the maleimido groups on the glass plate surface and the thiol groups at the terminus of the nucleic acid probes. The amount of the DNA solution ejected by one ejection operation of the printer was about 24 pl.

(5) Blocking Reaction

After completion of the reaction between the maleimido group and the thiol group, the glass plate was washed with an 1 M NaCl/50 mM phosphate buffer solution (pH 7.0) to rinse completely away the liquid containing DNA on the surface of the glass plate. Then, the glass plate was immersed in a 2% bovine serum albumin aqueous solution and left for 2 hours to proceed a blocking reaction.

(6) Hybridization Reaction

A ssDNA with a base sequence complementary to DNA of SEQ ID No. 1 was synthesized using an automatic DNA synthesizer, and rhodamine was bound to its 5'-terminus to obtain a labeled ssDNA. This labeled ssDNA was dissolved in 1 M NaCl/50 mM phosphate buffer solution (pH 7.0) to a final concentration of 1 µM. The probe array subjected to the blocking treatment obtained in the above (5) was immersed in this solution at room temperature (25° C.) for 3 hours to proceed a hybridization reaction. Then, the probe array was washed with 1 M NaCl/50 mM phosphate buffer solution (pH 7.0) to wash away the ssDNA which had not been hybridized with the probe nucleic acid. Then, the fluorescence intensity of each spot of the probe array was quantified using the image analyzer (Product name: ARGUS; Hamamatsu Photonics Co., Ltd.).

(7) Results

The fluorescence intensity of the spots of the nucleic acid of SEQ ID No. 1 completely matched with the labeled ssDNA was 4,600. In addition, the probe array in which the respective spots emitted fluorescence after hybridization was observed using a fluorescent microscope (Nikon Corp.). The results indicated that, in the probe array of this example,
(a) Each spot was almost round and had a diameter in a range of about 70–100 µm;
(b) There were spaces of about 100 µm, which was almost the same as the diameter of each spot, between adjacent spots so that each spot was clearly independent;
(c) The columns and rows of the spots were arranged in lines.

These facts are very effective in automatic detection, etc. of hybridized spots on a probe array.

EXAMPLE 2

Manufacturing of Nucleic Acid Probe Array Using Bubble Jet Printer and Detection of Target Nucleic Acid Using the Probe Array (1) A glass plate for a probe array was prepared in the same manner as in (1) and (2) of Example 1.

(2) Synthesis of Probe DNA

Single-stranded nucleic acids of SEQ ID Nos. 1–4 were synthesized using an automatic DNA synthesizer. The ss nucleic acids of SEQ ID Nos. 2–4 were as follows: from the ss nucleic acid of SEQ ID No. 1 used in Example 1, one base differs in SEQ ID No.2, 3 bases in SEQ ID No. 3, and 6 bases in SEQ ID No. 4. A thiol (—SH) group was introduced at each terminus of the ssDNAs of SEQ ID Nos. 1–4 using Thiol-Modifier (Glen Research Co., Ltd.) during synthesis on the automatic DNA synthesizer. Following ordinary deprotection, DNA was then recovered, purified with high performance liquid chromatography, and used in the following experiments. The sequences of SEQ ID Nos. 2–4 are shown below:

SEQ ID No. 2:
$5'$HS–$(CH_2)_6$–O–$PO_2$–O–ACTGGCCGTT̲GTTTTACA$3'$

SEQ ID No. 3:
$5'$HS–$(CH_2)_6$–O–$PO_2$–O–ACTGGCCGC̲T̲T̲TTTTACA$3'$

SEQ ID No. 4:
$5'$HS–$(CH_2)_6$–O–$PO_2$–O–ACTGGCA̲T̲C̲T̲T̲GTTTACA$_3$.

(3) DNA Probe Ejection and Binding to Substrate Using BJ Printer

The ssDNAs of SEQ ID Nos. 1–4 above were used to prepare 4 ejection liquids by the method similar to that described in (4) of Example 1. The respective liquids were filled in 4 ink tanks of a bubble jet printer used in Example 1 and the respective ink tanks were mounted on the bubble jet heads. The glass plate prepared in (1) was mounted on the printer, and the 4 nucleic acid probes were spotted in respective 4 areas of 3×3 mm on the glass plate. The spotting pattern in each area was the same as that in Example 1. After completion of spotting, the glass plate was left in a humidified chamber for 30 minutes to react the maleimido group and the thiol group.

(4) Blocking Reaction

After completion of the reaction between the maleimido group and the thiol group, the glass plate was washed with a 1 M NaCl/50 mM phosphate buffer solution (pH 7.0) to rinse completely away the solution containing DNA on the surface of the glass plate. Then, the glass plate was immersed in a, 2% bovine serum albumin aqueous solution and left for 2, hours to proceed a blocking reaction.

(5) Hybridization Reaction

A ssDNA with a base sequence complementary to DNA of SEQ ID No. 1 was synthesized using an automatic DNA synthesizer, and rhodamine was bound to its 5'-terminus to obtain a labeled ssDNA. This labeled ssDNA was dissolved in an 1 M NaCl/50 mM phosphate buffer solution (pH 7.0) to a final concentration of 1 µM. The probe array obtained in (4) was subjected to a hybridization reaction for 3 hours. Then, the probe array was washed with 1 M NaCl/50 mM phosphate buffer solution (pH 7.0) to wash away the ssDNA which had not been hybridized with the probe nucleic acid. Then, the respective spots of the probe array were observed using a fluorescent microscope (Nikon Corp.) and the amounts of fluorescence were quantified using the image analyzer (Product name: ARGUS; Hamamatsu Photonics Co., Ltd.).

(6) Results

The fluorescence intensity of the spots of the DNA probe of SEQ ID No. 1 completely matched with the labeled ssDNA was 4,600, while the fluorescence intensity was 2,800 for the spots of the DNA probe of SEQ ID No. 2 containing one mismatched base. For the spots of the DNA probe of SEQ ID No. 3 having 3 mismatched bases, the fluorescence intensity was 2,100, which was less than half that for the completely matched probe. No fluorescence was observed for DNA of SEQ ID No. 4 containing 6 mismatched bases. The above result indicates that a completely complementary ssDNA was specifically detected on the DNA array substrate.

EXAMPLE 3

Concentration of DNA Probe Solution and Bubble Jet Ejection Properties (1) Synthesis of DNA Probe A ssDNA of SEQ ID No. 5 shown below was synthesized using an automatic DNA synthesizer and dissolved in a TE solution (10 mM Tris-HCl (pH 8)/mM EDTA aqueous solution) to concentrations of about 0.2 mg/ml, 2 mg/ml, and 1.5 mg/ml to prepare DNA probe solutions of 3 different concentrations (accurate concentrations were calculated from absorbance).

SEQ ID No. 5:

5'GCCTGATCAGGC3'

(2) Ejection by BJ Printer

An aqueous solution containing glycerin at 7.5 wt %, urea at 7.5 wt %, thiodiglycol at 7.5 wt %, and acetylene alcohol (Product name: Acetylenol EH; Kawaken Fine Chemical Co., Ltd.) having the above general formula (I) at 1 wt % was prepared, added to the 0.2 mg/ml probe solution prepared in (1), and adjusted a final concentration to about 0.02 mg/ml (3 $\mu$M). This solution was filled in an ink tank of a bubble jet printer used in Example 1 and the ink tank was mounted on a bubble jet head used in Example 1.

An aluminum plate of A4 size was mounted on the printer and the liquid was spotted to an area of 3×5 square inch of the aluminum plate. The condition of spotting was set so as to perform spotting in a density of 360×720 dpi in the above area. A commercial ink for BJ620 was first printed on the aluminum plate as a control. This operation was performed on a total of 4 aluminum plates.

The nucleic acid probe spotted on the respective aluminum plates was recovered using the TE solution and purified by a gel filtration method. The amounts of the recovered nucleic acid probe purified were measured by absorbance. The recovery of the nucleic acid probe theoretically obtained is as follows. That is, a volume of a droplet ejected from the head of the printer used in this example was 24 picoliters. Then, since there were 4 aluminum plates on which the solution was spotted in an area of 3×5 square inch at a density of 360×720 dpi, the following equation was obtained:

24 (picoliters)×(720×360)×(3×5)×4 plates=373 $\mu$l

Figure 3:
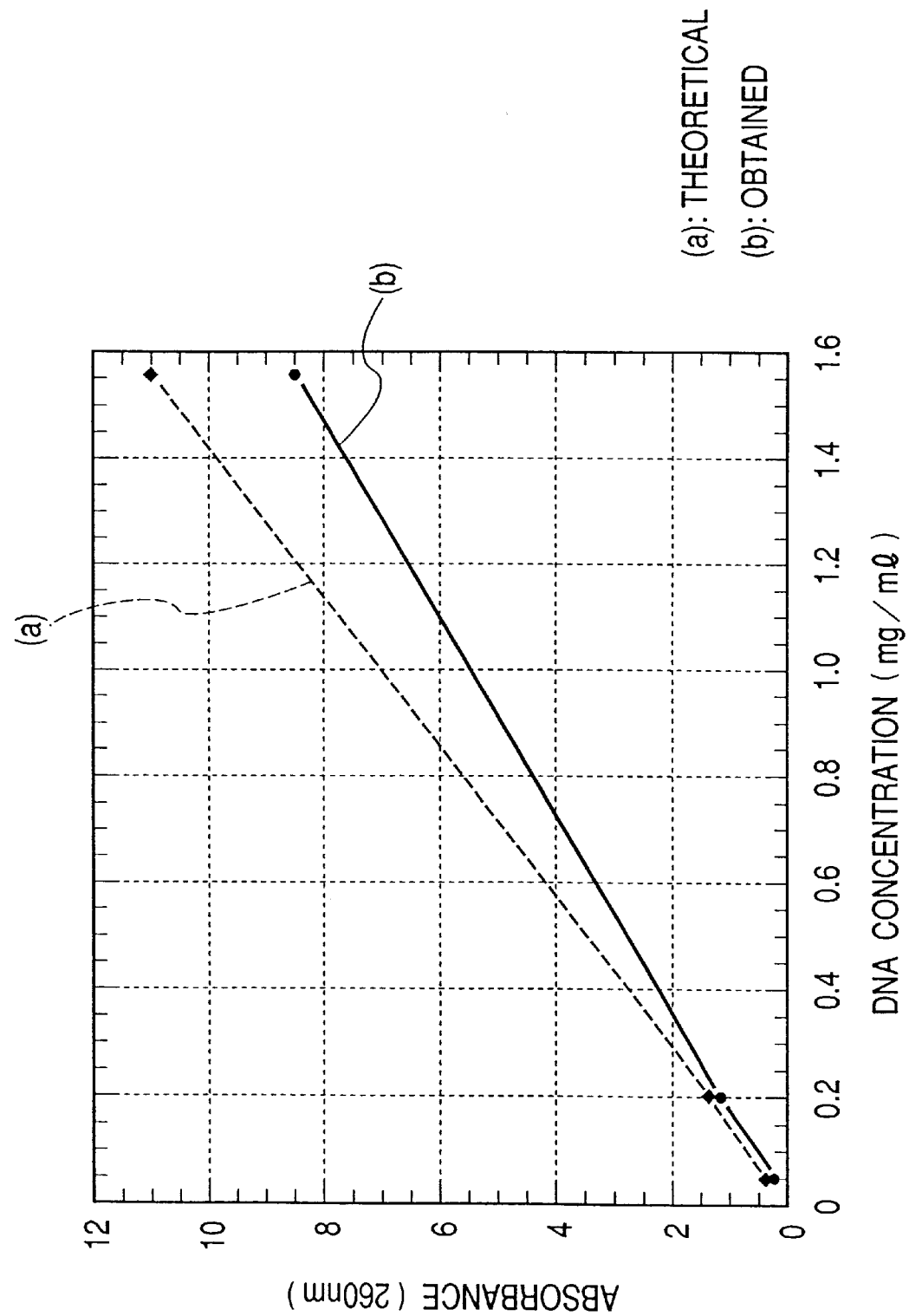
FIG. 3 shows a graph comparing a theoretical amount and an actual recovery of a nucleic acid probe spotted on an aluminum plate by the bubble jet method in Example 3.

Absorbance at 260 nm of the probe nucleic acid for this volume and absorbance at 260 nm of recovered nucleic acid probe are shown in FIG. 3.

(3) The operation identical to that described in (2) was performed on the probe solutions at concentrations of 2 mg/ml and 15 mg/ml. The final concentrations of the nucleic acid probe of the respective ejection liquids were 30 $\mu$M (0.2 mg/ml) and 225 $\mu$M (1.5 mg/ml).

Absorbance of the probe nucleic acid recovered from the respective solutions and absorbance of the probe nucleic acid in amounts theoretically obtained are shown in FIG. 3.

(4) Results

As shown in FIG. 3, the amounts of a nucleic acid probe actually ejected were close to the values theoretically anticipated. From this, in ejection of a nucleic acid probe using the bubble jet method, no quantitative loss of the nucleic acid probe due to burning and sticking of the nucleic acid probe to the heater of the bubble jet head was observed. No troubles in the head, such as no ejection, occurred during the step of spotting on the aluminum plate using liquids of various concentrations. A macroscopic comparison with the spots of the ink for a bubble jet printer spotted on the aluminum plate as a control and the spots of the nucleic acid probe showed that the spotting status for the spots formed using the liquids at concentrations of 3 $\mu$M and 30 $\mu$M was similar to that for the ink spot. The spots formed using the liquid at a concentration of 225 $\mu$M exhibited some disorders as compared with the ink spot.

EXAMPLE 4

Influence of Bubble Jet Process on Nucleic Acid Probe (1) Synthesis of Nucleic Acid Probe A nucleic acid probe comprised of 10 mer adenylic acids (abbreviated as "A" hereinafter) (synthetic substance), oligoA (40–60 mer; Pharmacia Co., Ltd.), and poly(da) (300–400 mer; Pharmacia Co., Ltd.) were respectively diluted with a TE solution to prepare solutions of the nucleic acid probes of different base lengths at a final concentration of 1 mg/ml. The base sequence of the 10-mer probe (SEQ ID No. 6) is shown below:

SEQ ID No. 6:

5'AAAAAAAAAA3'

(2) Ejection of DNA Solution with Bubble Jet Printer

An aqueous solution containing glycerin at 7.5 wt %, urea at 7.5 wt %, and acetylene alcohol (Product name: Acetylenol EH; Kawaken Fine Chemical Co., Ltd.) shown by the general formula (I) at 1 wt % was prepared and the respective nucleic acid probe solutions prepared in (1) were diluted with this aqueous solution to a final concentration of 0.1 mg/ml.

As in Example 3, the respective nucleic acid probe solutions filled in a cartridge were ejected on an aluminum plate and the spotting status was macroscopically observed. As a result, for the nucleic acid probes with base lengths of 10 mer and 40–60 mer, probe arrays had independent spots arranged in order on the aluminum plate. As for the nucleic acid probe of 300–400 mer, although a similar array was obtained fundamentally, adjacent spots connected in some parts. This is considered to occur due to slightly inaccurate ejection direction of the bubble jet head caused by the changes in physical properties attributable to a long base chain of the nucleic acid probe.

Figure 4:
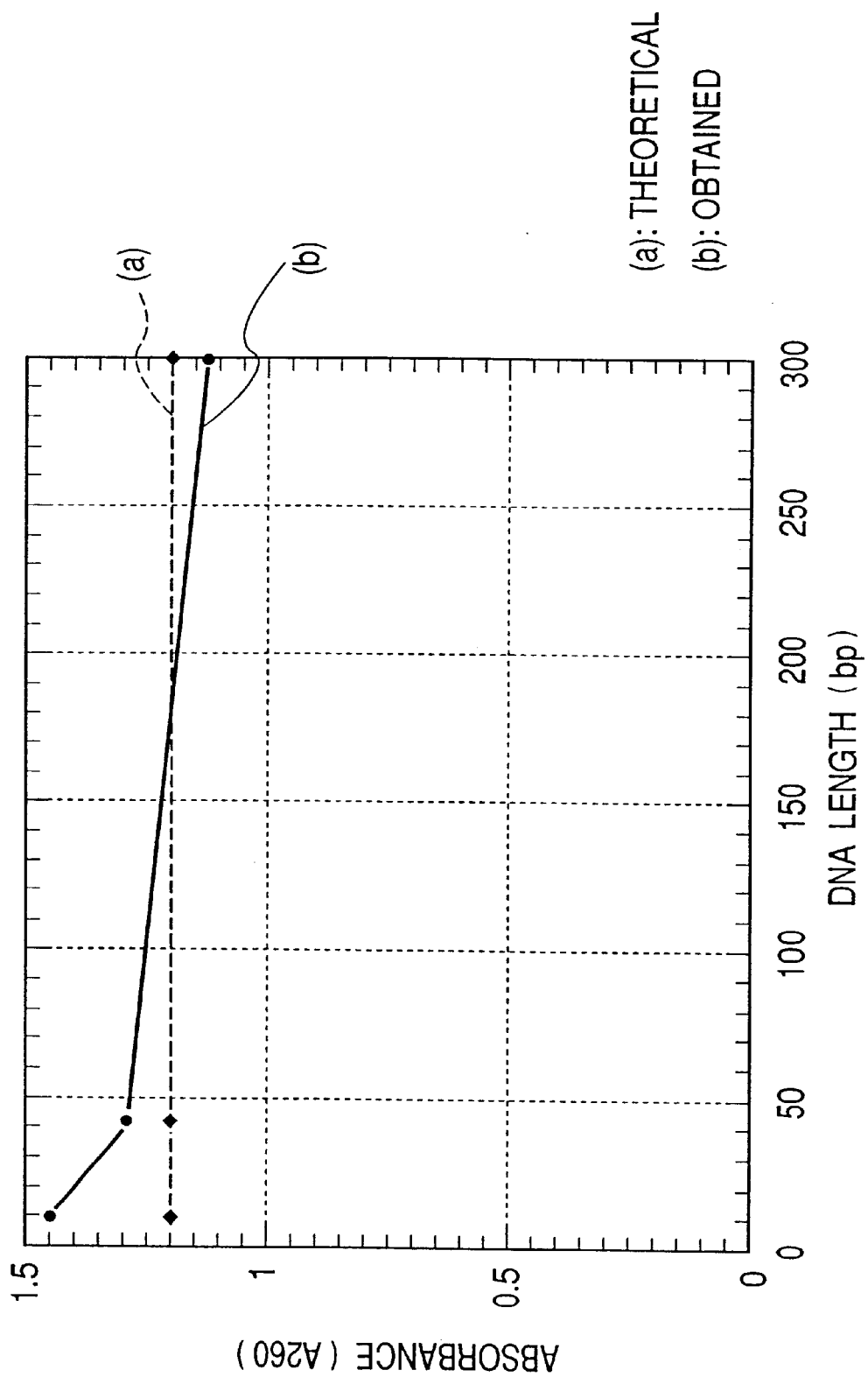
FIG. 4 shows a graph comparing a theoretical amount and an actual recovery of a nucleic acid probe spotted on an aluminum plate by the bubble jet method in Example 4.

The spots on the probe array prepared using the respective nucleic acid probe solutions were recovered as described in Example 3. A 100 $\mu$l aliquot of each recovered nucleic acid probe solution was analyzed by reverse phase HPLC, and whether or not the nucleic acid probes were cleaved by ejection in comparison with the solutions before ejection. A 7–70% gradient of acetonitrile containing 1 M triethylamine acetate was used as an eluent for the reverse support HPLC. As a result, no DNA fragment considered due to cleavage was observed, confirming that the nucleic acid probes were not denatured by ejection by the bubble jet method. The recovered nucleic acid probes were quantified as in Example 3 and the nucleic acid probes with 3 different base lengths were recovered almost at theoretical values as shown in FIG. 4.

EXAMPLE 5

Investigation of Reaction Time

Probe arrays were prepared as in Example 1, except that the glass plate subjected to surface treatment on which the nucleic acid probes were spotted were left in a humidified chamber at room temperature (25° C.) for 10 minutes or 90 minutes, or overnight in (4) of Example 1. The respective arrays were used for hybridization. As a result, the probe arrays reacted for 90 minutes or overnight exhibited fluorescence strength similar to that shown by the probe array obtained in Example 1. It indicates that a binding reaction between the maleimido group on the surface of the glass plate and the thiol group of the terminus of the nucleic acid probe almost completed in 30 minutes. The probe array reacted for 10 minutes, however, exhibited fluorescence about 70% of that in Example 1.

EXAMPLE 6

Manufacturing of PNA Probe Array Using Bubble Jet Printer and Detection of Target Nucleic Acid Using the Probe Array (1) A glass plate for probe array was prepared in the same manner as in (1) and (2) of Example 1.

(2) Synthesis of Probe PNA

Protein nucleic acids (PNAs) (Nippon Perceptive Co., Ltd.) with the base sequences of SEQ ID Nos. 7 and 8 shown below were prepared. In the PNAs, a cysteine residue (expressed as Cys) was bound to the N-terminus of PNA (corresponding to 5'-terminal of DNA) and, as a result, a thiol group was introduced at the N-terminus. The PNA probe of SEQ ID No.8 is obtained by changing one base of the PNA probe of SEQ ID No. 7.

SEQ ID No. 7
$^N$Cys-
NH(CH$_2$)$_2$-O-(CH$_2$)$_2$-O-CH$_2$CONH-ACTGGCCGTCGTTTTACA$^C$

SEQ ID No. 8
$^N$Cys-
NH(CH$_2$)$_2$-O-(CH$_2$)$_2$-O-CH$_2$CONH-ACTGGCCGT$\underline{T}$GTTTTACA$^C$ (3) PNA Probe Ejection and Binding to Substrate Using BJ Printer The respective PNA probes were dissolved in 100 µl of 0.1 wt % trifluoroacetic acid to a final concentration of 80 µM. Then, an aqueous solution containing glycerin at 7.5 wt %, urea at 7.5 wt %, thiodiglycol at 7.5 wt %, and acetylene alcohol (Product name: Acetylenol EH; Kawaken Fine Chemical Co., Ltd.) shown by the above general formula (I). at 1 wt % was added to the trifluoroacetic acid solutions of the PNAs to adjust a final concentration of PNA probe to 8 µM. These liquids had surface tension in a range of 30–50 dyn/cm and viscosity in a range of 1–5 cps.

These PNA probe solutions were spotted, in a manner similar to that described in (3) of Example 2, on the respective areas of the glass plate prepared in (1). After completion of spotting, the glass plate was left standing in a humid chamber for 3 hours to react the maleimido group and the thiol group. The amount of the PNA probe solution ejected by one ejection operation of the printer was about 24 pl.

(4) Blocking Reaction

After completion of the maleimido group and the thiol group, the glass plate was washed with an 1 M NaCl/50 mM phosphate buffer solution (pH 7.0) to rinse completely away the liquid containing PNA on the surface of the glass plate. Then, the glass plate was immersed in a 2% bovine serum albumin aqueous solution and left for 3 hours to proceed a blocking reaction (5) Hybridization Reaction A ssDNA having a base sequence complementary to the PNA of SEQ ID No. 7 was synthesized using an automatic DNA synthesizer, and rhodamine was bound to its 5'-terminus to obtain a labeled ssDNA. This labeled ssDNA was dissolved in 10 mM phosphate buffer solution (pH 7.0) to a final concentration of 5 nM (solution volume of 1 ml). The PNA probe array subjected to the blocking treatment in the above (4) was immersed in this solution at room temperature (25° C.) for 12 hours to proceed a hybridization reaction. Then, the probe array was washed with a 10 mM phosphate buffer solution (pH 7.0) to wash away the ssDNA which had not been hybridized with the PNA probe. Then, an amount of fluorescence of spots of the probe array was quantified using the image analyzer (Product name: ARGUS 50; Hamamatsu Photonics Co., Ltd.).

(6) Results

The fluorescence intensity of each spot of the PNA probe of SEQ ID No. 7 completely matched with the labeled ssDNA was 2,400, whereas it was 1,100, about half, for the PNA probe of SEQ ID No. 8 having one mismatched base. From this, the completely complementary ssDNA was specifically detected on the PNA array.

After hybridization, the probe array in which each spot emits fluorescence was observed with a fluorescent microscope (Nikon Corp.). As a result, in the probe array of this example, it was indicated that (a) Each spot was almost round and had a diameter in a range of about 200 µm;

(b) There were distinct spaces of about 50 µm, between adjacent spots so that each spot was clearly independent;

(c) The columns and rows of the spots were arranged in lines.

These facts are very effective in automatic detection, etc. of hybridized spots on a probe array.

In addition, since it is not necessary for a solution used at the hybridization reaction and subsequent removal of unreacted ssDNA to contain sodium chloride, it is not required to pay attention on deposition of sodium chloride during observation of fluorescence. As a result, detection of hybrids on a probe array could be detected more easily. In addition, it is not necessary to seal tightly during storage and handling is easier.

A reason for a diameter of the spots of the PNA probe being larger than that of the spot of the probe array obtained in Example 1 has not bee clarified. However, the present inventors obtained a finding that PNA probes had slightly inferior water-solubility as compared with DNA probes. It is thus assumed that spot diameters differed, since the difference in water-solubility causes difference in surface tension of the respective ink jet ejection liquids.

EXAMPLE 7

Preparation and Evaluation of Glass Substrate with Black Matrix Used for Probe Array Which Has Epoxy Groups Introduced to Its Surface (1) A glass substrate (50 mm×50 mm) consisting of synthetic quartz was subjected to ultrasonic cleaning with a 2 wt % sodium hydroxide aqueous solution and to UV ozonization for surface cleaning. A 50 wt % methanol aqueous solution containing 1 wt % of silane coupling agent (Product name: KBM403, from Shin-Etsu Chemical Co., Ltd.), which contains a silane compound having an epoxy group (γ-glycidoxypropyltrimethoxysilane), was stirred at room temperature for 3 hours so as for the methoxy groups of the above silane compound to be hydrolyzed. Then the solution was applied to the surface of the above substrate with a spin coater, heated at 100° for 5 minutes, and dried to introduce epoxy groups to the surface of the substrate.

(2) Then DEEP-UV resist (nega-type resist for black matrix) (Product name: BK-739P, from Nippon Steel Chemical Co., Ltd.) containing carbon black was applied to the above substrate with a spin coater to yield a film thickness of 5 µm after setting, and the substrate was heated at 80° for 5 minutes using a hot plate for film setting. An area of 1 cm×1 cm of the substrate was subjected to proximity exposure using a mask which was patterned so that the distance (X) between the adjacent wells in FIG. 5 would be 100 µm and the geometry of the wells would be a square of 100 µm×100 µm, and the substrate was developed in an inorganic alkaline developing solution using a spin developing instrument, then washed with distilled water to completely remove the developing solution. The substrate was then roughly dried using a spin drier and heated at 180° C. for 30 minutes in a clean oven for its resist to be fully set; thus, a substrate having 2500 wells arranged in a prescribed arrangement where the adjacent wells are isolated from each other by black matrix was obtained. Here the calculated volume of each well was 50 picoliters (pl).

At this point, the black matrix surface was hard to get wet since its contact angle to water was 93°, and the bottom surface of the wells was easy to get wet since its contact angle to water was 35°.

(3) A 10 µM Rhodamine B aqueous solution was filled into an ink tank for a bubble jet printer (Product name: BJC620, from Canon Inc.) and the ink tank was fitted to the bubble jet head of the bubble jet printer used in Example 1 described above. And the solid supports prepared in the above description (1) and (2) were set in the printer and the wells of each solid support were supplied with Rhodamine B so as to make a checkered pattern. Here the supply of Rhodamine B per well was about 50 pl, and the delivery positioning accuracy of this printer was ±2.5 µm. Then a 10 µM amino-FITC aqueous solution was filled into another ink tank, the ink tank was fitted to the bubble jet head of the above printer, and the solution was supplied to those wells other than and adjacent to the wells already supplied with Rhodamine B. The reason for employing Rhodamine B and amino-FITC is that they are water-soluble, they are easy to deliver from an ink jet head, and that observation of their fluorescence allows to check the conditions and cross-contamination of the solution supplied to the wells.

(4) A G excitation filter (for Rhodamine B) and a B excitation filter (for amino-FITC) were set in a fluorescence microscope (from Nikon Corporation), and the conditions of each solution supplied to the wells were observed from their fluorescence at a magnification of×100. The results showed that each solution was supplied to the wells uniformly without forming a drop. In addition, no fluorescence of the other's pigment was observed in every well, that is, no cross-contamination was observed.

EXAMPLE 8

Preparation of Probe Array Using the Substrate of Example 7 and Detection of Target Nucleic Acid Therewith (1) A substrate with a BM was prepared in the same manner as in Example 7.

(2) As DNA probes, three oligonucleotides were prepared, that is, a 18 mer oligonucleotide whose 5' terminus hydroxyl group was linked with an amino group via a phosphate group and a hexamethylene (SEQ ID No. 9), a probe differing from the oligomer of SEQ ID No. 9 in a single nucleotide (SEQ ID No. 10), and a probe differing from the oligomer of SEQ ID No. 9 in two nucleotides (SEQ ID No. 11) (all of these are HPLC grade, from Nippon Flour Mills Co., Ltd.). The base sequence of the oligomer of SEQ ID No. 9 was complementary to that of a part of the multiple cloning site of M13mp18-ss DNA which is a ssDNA. The base sequence and the linkage structure of the DNA probes of SEQ ID Nos. 9–11 are shown below.

```
SEQ ID No. 9
5'NH2-(CH2)6-O-PO2-O-TGTAAAACGACGGCCAGT 3'

SEQ ID No. 10
5'NH2-(CH2)6-O-PO2-O-TGTAAAACCACGGCCAGT 3'

SEQ ID No. 11
5'NH2-(CH2)6-O-PO2-O-TGTATAACCACGCCCAGT 3'
```

(3) Single-stranded DNAs were synthesized each of which was fully complementary to each of the DNA probes of SEQ ID Nos. 9–11. Then each DNA probe and each ssDNA were dissolved separately in a TE solution (pH 8) whose NaCl concentration was 50 mM to yield a final concentration of 100 µM; thus, DNA prove solutions and complementary ssDNA solutions were prepared. 100 µl of each DNA probe solution was added to and mixed with 100 µl of the corresponding complementary ss DNA solution, and each mixture was heated to 90° C., and then cooled to 25° over 2 hours to cause the DNA probe and the ss DNA to hybridize. Each of the solutions containing a hybrid of each of the DNA probes of SEQ ID Nos. 9–11 was added to the aqueous solution containing 7.5 wt % of glycerol, 7.5 wt % of urea, 7.5 wt % of thiodiglycol and 1 wt % of acetylene alcohol represented by the general formula (1) above (Product name: Acetylenol EH, from Kawaken Fine Chemical, Co., Ltd.) to a final hybrid concentration to 8 µM. The surface tension of each solution containing a hybrid of each DNA probe lies in the range of 30 to 50 dyne/cm, and the viscosity in the range of 1 to 5 cps (E-type viscometer, from Tokyo Keiki, Co., Ltd.).

Figure 6:
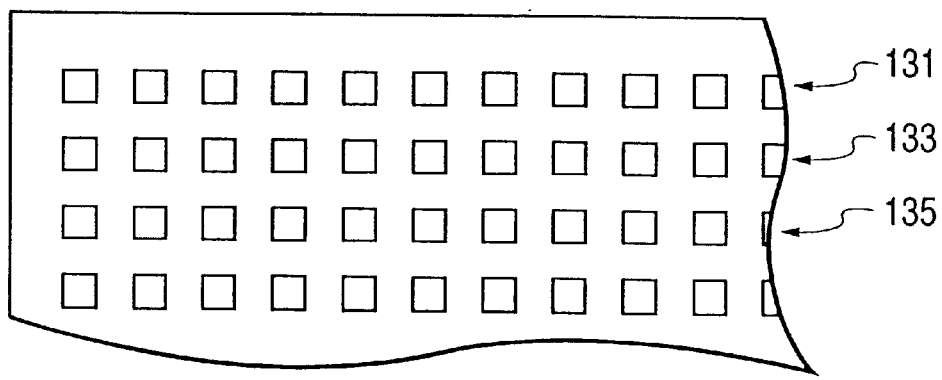
FIG. 6 is to explain a spotting method in Example 8.

Then three ink tanks for a bubble jet printer (Product name: BJC620, from Canon Inc.) were prepared, and each ink tank was filled with each of the above three different hybrid solutions and fitted to the head of the bubble jet printer used in Example 1. The glass substrate with a black matrix (BM) prepared in the above description (1) and (2) was also set in the printer, and the solution containing the hybrid of the DNA probe of SEQ ID No. 9 was first supplied to the first column of the wells (131 in FIG. 6). Then the solution containing the hybrid of the DNA probe of SEQ ID No. 10 was supplied to the second column of the wells (133 in FIG. 6) which were adjacent to those of the first column, and further the solution containing the hybrid of the DNA probe of SEQ ID No. 11 was supplied to the third column of the wells (135 in FIG. 6) which were adjacent to those of the second column. Four ejections of each hybrid solution were supplied to each well to bring the final amount of the solution per well to about 100 pl. This amount was about 2 times as large as the volume of each well; however, the microscopic observation of the wells revealed that, although the hybrid solution supplied rose above the surface more than the opening of the wells, it remained in the wells due to the hydrophobic matrix, and cross-contamination between the wells was not observed.

Then the substrate was placed in a thermohygrostat whose temperature and humidity were 25° and 100%, respectively, to react amino groups of the probes with epoxy groups of the wells. Since the amino groups in the bases of the probes hybridized with ssDNAs completely complementary to them, they would not react with epoxy groups of the wells.

(4) Then the substrate was washed with 80° C. pure water for 10 minutes to dissociate the complementary strands from the probes linked to the substrate and wash them away. After that, the substrate was treated with a 1% ethanolamine aqueous solution at room temperature for 1 hour to open the rings of the unreacted epoxy groups of each well. The substrate was then washed with pure water and dried.

The operation in the above description (4) allows to open the rings of the epoxy groups unreacted with the DNA probes in the wells to give hydroxyl groups, and the reacted ethanolamine also has a hydroxyl group; therefore, the hydrophilicity of the bottom surface of the wells is increased, which is advantageous when a solution containing target ssDNAs is supplied to the wells.

(5) Single-stranded DNAs fully complementary to the DNA probe of SEQ ID No. 9 were dissolved in TE solution (pH 8) whose NaCl concentration was 50 mM to yield a final concentration of 10 $\mu$M, and after the probe array of the wells obtained in the above description (4) to which epoxy groups were introduced was immersed in the solution, the temperature of the mixture was decreased from 80° C. to 25° C. over two hours to cause a hybridization reaction. After that, the substrate was washed at 20° C. for 20 minutes with TE buffer solution (pH 8) whose NaCl concentration was 10 mM, and the washing solution remained on the surface of the substrate was removed with a spin drier.

(6) 2-methyl-4,6-bis(4-N,N-dimethylaminophenyl)pyrylium iodide (hereinafter referred to as P2), which does not fluoresce until it is intercalated into a double-stranded nucleic acid, was dissolved in a TE solution (pH 8.0) whose NaCl concentration was 50 mM to yield a final concentration of 10 $\mu$M. And this solution was filled into the ink tank of the above ink jet printer and the tank was fitted to the head of the above ink jet printer. The substrate subjected to hybridization in the above description (5) was also set in the above printer and each well of the substrate was supplied with 100 pl of P2 solution. After that, the substrate was allowed to stand in a special chamber whose humidity was 100% for 5 minutes to avoid getting dried, while its fluorescence was observed and quantitatively determined using an inverted microscope (Product name: IMT2, from Olympus Optical Co., Ltd., magnification:×100, using a filter cube for a fluorescence microscope (an excitation filter of 455 nm to 595 nm (passing), a dichroic mirror of 620 nm, a barrier filter for fluorescence of 610 nm to 725 nm (passing) with an ICCD camera (Product name: C2400-87, from Hamamatsu Photonics Co., Ltd) and an image processor (Product name: ARGUS 50, from Hamamatsu Photonics Co., Ltd) connected to it. The observation area was set at 25 $\mu$m×25 $\mu$m and the integration×64, and the amplification level of ARGUS 50 was set appropriately.

As a result, fluorescent intensity of 1200 to 1500 which was almost the same as that of the background was observed from the wells to which the DNA probe of SEQ ID No. 11 was bonded, while fluorescent intensity of 9800 to 10300 was observed from the wells having the DNA probe of SEQ ID No. 9 and fluorescent intensity of 3500 to 3900 was observed from the wells having the DNA probe of SEQ ID No. 10. Measurement of fluorescent intensity was made again after each solid support was washed at 35° C. for 10 minutes with a TE buffer solution, and the fluorescent intensity from the wells containing the DNA probe of SEQ ID No. 10 decreased to the background level.

These results show that the use of the probe array according to the present invention allows to achieve a hybridization reaction in each well, in addition, to specifically detect the target nucleic acid which is completely complementary to the DNA probe of SEQ ID No. 9.

EXAMPLE 9

Selective Supply of Reactants to Each Well of the Probe Array of Example 8 and Reaction Thereof with Probe (1) A substrate holding immobilized DNA probes of SEQ ID Nos. 9–11 was prepared in the same manner as in Example 8.

(2) Three types of ssDNAs were synthesized each of which was completely complementary to one of the DNA probes of SEQ ID Nos. 9–11. Each ssDNA was dissolved in a TE buffer solution (pH 8) containing 50 mM NaCl, to a final concentration of 100 $\mu$M. Three ink tanks for a bubble jet printer (Product name: BJC620, from Canon Inc.) were prepared, and three tanks were filled with the above ssDNA solutions respectively and fitted to the bubble jet printer head used in Example 1. The substrate prepared in the above description (1) was also set on the printer, and to each well where one of the DNA probes of SEQ ID Nos. 9–11 was immobilized, 100 pl/well of the solution containing the corresponding complementary ssDNA was supplied. From the microscopic observation of the well conditions at this point, neither solution oozing nor cross-contamination was observed, showing that plural reaction solutions can be supplied separately to the wells of the probe array.

(3) After hybridization reaction was carried out in each well in the same manner as in Example 8, a P2 solution was supplied to each well in the same manner as in Example 8 to detect the formed hybrid by the observation of fluorescence. As a result, fluorescent intensity of 9800–10300 was observed in each well. It was confirmed from the result that reactant can be supplied separately to each well of the probe array, the reactant can react with the probe in each well, and that the resultant product of the reaction can be detected.

EXAMPLE 10

Treatment for Providing Hydrophilicity to the Bottom Surface of the Substrate Wells of Example 7

(1) A glass substrate with a black matrix pattern was prepared in the same manner as in Example 7.

(2) The surface of the substrate on which a black matrix was formed was subjected to UV ozonization. At this point, the contact angle of the surface of the black matrix to water was 93°0, which means that the surface of the black matrix was water-repellant, and the contact angle of the bottom surface of the wells to water was 22°, which means that the bottom surface of the wells was hydrophilic compared with the untreated bottom surface of the wells of the substrate prepared in Example 7. This may be attributed to the effect of UV ozonization described above.

(3) Then Rhodamine B and amino-FITC aqueous solutions, just as in Example 7, were fed to the wells from an ink jet printer, and the conditions in the wells were observed. The observation showed that each aqueous solution spread uniformly not forming a drop within the wells. When a solid support having wells on its surface is used as a solid support of a probe array, it is not necessary to hold the solution ejected from an ink jet printer at a very definite position on the surface of the support, and fully spreading of the ejected solution over the bottom surface of the well is preferable for the subsequent detection of the reaction between a probe and a target substance The treatment for making the bottom surface of the well hydrophilic, which was described in this example, is a preferred embodiment of the present invention. Furthermore, there was found only expected pigment in each well, showing that, with this ink jet process, each aqueous pigment solution can be supplied to each well without causing any cross-contamination.

EXAMPLE 11

Process for Preparing Probe Array Using Solid Support Containing Functional Groups for Probe Immobilization Introduced by Supplying Solution by Ink Jet Method in Each Well in Black Matrix and Its Use (1) A substrate with a black matrix was prepared in the same manner as in Example 7.

(2) A silane coupling agent (Product name: KBM603, from Shin-Etsu Chemical Co., Ltd.) which contained a silane compound to which an amino group Is bonded (N-β-(aminoethyl)-γ-aminopropyltrimethoxysilane) was dissolved in a 10 wt % methanol aqueous solution to the concentration of 1 wt %, and stirred at room temperature for 3 hours to hydrolyze methoxy groups of the above silane compound. Then this solution was filled into an ink tank for a bubble jet printer (Product name: BJC620, from Canon Inc.), and the tank was fitted to the head of the bubble jet printer used in Example 1. The substrate prepared in the above description (1) was also set on the printer, and the solution of the silane coupling agent, which contained a silane compound whose methoxy groups had been already hydrolyzed, was supplied to each well of the substrate in the same manner as in Example 8. After left standing in a thermohygrostat whose temperature and humidity were 25° C. and 100%, respectively for 30 minutes, the substrate was washed with distilled water, spin-dried, and baked at 100° C. for 30 minutes to introduce amino groups to the bottom surface of the wells.

(3) Then succiimidyl-4-(maleimidophenyl)butylate (from Aldrich Co., Ltd.) was dissolved in a 5 wt % DMSO solution to yield a final concentration of 5 wt %, and 100 pl of this solution was supplied to each well using a ink jet printer in the same manner as the above description (2), after that, the substrate was allowed to stand in a thermohygrostat whose temperature and humidity were 30° C. and 100% respectively for 2 hours. The substrate was then washed with distilled water, and spin-dried. Thus maleimido groups were introduced to the bottom surface of the wells.

(4) As DNA probes, three oligonucleotides were prepared, that is, a 18mer oligonucleotide whose 5' terminus hydroxyl group was linked to a thiol group via a phosphoric group and hexamethylene (SEQ ID No. 12), a probe differing from the oligomer of SEQ ID No. 12 in a single nucleotide (SEQ ID No. 13), and a probe differing from the oligomer of SEQ ID No. 12 in two nucleotides (SEQ ID No. 14) (all of these are HPLC grade, from Nippon Flour Mills Co., Ltd.). The base sequence and the linkage structure of the DNA probes of SEQ ID Nos. 12–14 are shown below.

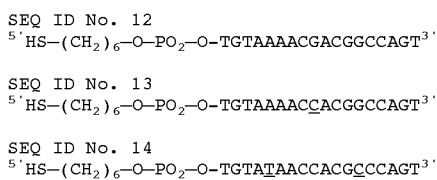

(5) Each of the above DNA probes of SEQ ID Nos. 12–14 were dissolved in a 10 mM phosphate buffer solution to yield a final concentration of 100 μM, and each DNA probe solution was supplied to the wells of the substrate prepared in the above description (3) in the same manner as in Example 8 described above. An microscopic observation of each well showed that the DNA probe solution supplied was rising above the surface of the opening of the well, but remained in the wells due to the hydrophobic matrix, and cross-contamination between wells was not observed. After the substrate was allowed to stand on a thermohygrostat whose temperature and humidity were 30° C. and 100%, respectively, for 2 hours, it was washed with distilled water, spin-dried to allow thiol groups of each DNA probe to react with maleimido groups of each well to link the DNA probes to the substrate.

(6) Single-stranded DNAs were synthesized which were fully complementary to the DNA probe of SEQ ID No. 12. Then the ssDNAs were separately dissolved in a TE solution whose NaCl concentration was 50 mM to yield a final concentration of 10 μM. The substrate linked with the DNA probe obtained in the above description (5) was immersed in this solution, and its temperature was decreased from 80° C. to 25° C. over 2 hours to cause a hybridization. Then the substrate was washed at 20° C. for 20 minutes using a TE solution (pH 8) whose NaCl content was 10 mM, and the washing solution remained on the surface of the substrate was removed with a spin-drier.

(7) A reagent YOYO-1, which fluoresces when it intercalates in a hybrid, was dissolved in a TE solution whose NaCl concentration was 50 mM to yield a final concentration of 10 μM (pH 8). 100 pl of this solution was supplied to each well which had been subjected to the treatment in the above description (6), in the same manner as the above description (2) using an ink jet printer, and fluorescence was observed and quantitatively determined in the same manner as in Example 8 (using a B excitation filter). Here the signal amplification level of ARGUS 50 was the same as in Example 8.

As a result, fluorescent intensity of 1800 to 2000 which was almost the same as that of the background was observed in the wells containing the DNA probe of SEQ ID No. 14, while fluorescent intensity of 7500 to 8000 was observed in the wells containing the DNA probe of SEQ ID No. 12 and fluorescent intensity of 3100 to 3300 was observed in the wells containing the DNA probe of SEQ ID No. 13. After the solid support was washed at 35° C. for 10 minutes with a TE buffer solution, a measurement of fluorescent intensity of each well was made again, and the fluorescent intensity from the wells containing the DNA probe of SEQ ID No. 13 decreased to the background level.

These results shows that the use of a probe array according to the present invention allows to achieve a hybridization reaction in each well, in addition, to specifically detect the target nucleic acid which is completely complementary to the DNA probe of SEQ ID No. 9.

EXAMPLE 12

(1) A substrate was prepared to which the DNA probes of SEQ ID Nos. 12–14 were linked in the same manner as in Example 11.

(2) Three ssDNAs complementary to the DNA probes of SEQ ID Nos. 12–14 were synthesized. Then each DNA probe was dissolved in a TE buffer solution whose NaCl concentration was 50 mM to yield a final concentration of 10 $\mu$M. Here pH value of each ssDNA solution was 8. Three ink tanks for a bubble jet printer (Product name: BJC620, from Canon Inc.) were prepared, and three ink tanks were filled with the above three ssDNA solutions respectively and fitted to the head of the bubble jet printer used in Example 1. The substrate prepared in the above description (1) was also set on the printer, and to each well in which one of ssDNA probes of SEQ ID Nos. 12–14 was fixed, 100 pl/well of absolution containing corresponding complementary ssDNA was supplied. From a microscopic observation of the well conditions at this point, neither solution oozing nor cross-contamination was observed, showing that it is possible to supply the solution of the substances to be reacted separately to each well of the probe array.

(3) After hybridization reaction was carried out in each well in the same manner as in Example 11, a YOYO-1 solution was supplied to each well in the same manner as in Example 11 to detect hybrid formation by observing its fluorescence. As a result, fluorescent intensity of 7500–8000 was observed in each well. It was confirmed from this result that reactant could be supplied separately to each well of the solid support probe array and be reacted with the probe in each well, and that the resultant product of the reaction could be detected.

EXAMPLE 13

Process for Preparing a Probe Array Using a Substrate Provided with Wells Having Epoxy Groups Introduced by Immersing Substrate after BM Formation in a Solution for Epoxy Group Introduction (1) A substrate provided with a black matrix was prepared in accordance with the description (2) of Example 7.

(2) In the same manner as in (1) of Example 7, an 1 wt % aqueous solution of a silane coupling agent (Product name: KBM403, from Shin-Etsu Chemical Co., Ltd.), which contains a silane compound having an epoxy group ($\gamma$-glycidoxy propyl trimethoxysilane), was stirred at room temperature for 1 hour to hydrolyze methoxy groups of the silane compound molecule. Then the solid support prepared in the above description (1) was immersed in this solution at room temperature for 30 minutes and washed with distilled water, and after the remaining water was removed by nitrogen gas flow, it was baked at 120° C. for 5 minutes to introduce epoxy groups to the bottom surface of the wells. At this point, the black matrix surface was water-repellant since its contact angle to water was 95°, and the bottom of the wells was hydrophilic since its contact angle to water was 33°. Thus, introduction of epoxy groups to the bottom surface of the wells is also made possible by treating the BM-formed solid support with a silane coupling agent.

(3) In accordance with the procedures described in (3) and (4) of Example 8, the DNA probes, of SEQ ID Nos. 9–10 were bonded to the bottom surface of the wells.

(4) Single-stranded DNA complementary to the DNA probe of SEQ ID No. 9 was synthesized on an automatic DNA synthesizer, tetramethylrhodamine was bonded via a hexanolamine linker at its 5' terminus thereof to obtain a labeled ssDNA. Then the labeled ssDNA was dissolved in a TE buffer solution (pH 8) whose NaCl concentration was 50 mM to yield a final concentration of 2 $\mu$M. Subsequently, the DNA probe-bonding substrate prepared in the above procedure (3) was immersed into this solution, and the temperature of the solution was decreased from 80° C. to 25° C. over 2 hours to cause a hybridization reaction. After that, the probe array was washed at 29° C. for 20 minutes using 10 mM NaCl/TE buffer solution (pH 8) to wash away free labeled ssDNA.

Then the fluorescent intensity in each well was quantitatively determined in the same manner as in Example 8.

(5) Results

The fluorescent intensity of 8500–9400 was observed in the wells containing DNA probe of SEQ ID No. 9 which was a perfect match of the labeled ssDNAs. And the fluorescent intensity of 2800–3400 was observed in the wells containing the DNA probe of SEQ ID No. 10, while the fluorescent intensity of as low as 1200–1500 was observed in the wells linked with the DNA probes of SEQ ID No. 11. After the above probe array was washed at 35° C. for 10 minutes using a 10 mM NaCl/TE buffer solution (pH 8), the fluorescent intensity observed at the wells containing the DNA probe of SEQ ID No. 10 lowered to the level of the background. Thus, it is evident that the use of a probe array according to the present invention makes possible specific detection of target hybrid substances.

According to the present invention, as described above, a solution containing a probe can be spotted on a solid support without damaging the probe or without causing satellite spots by means of the ink jet method. The use of this method enables efficient manufacturing of a probe array of high quality comprising probe spots arranged independently in high density.

According to the present invention, a probe array to obtain more information about a target substance more accurately even from a small amount of a sample is also obtained. In addition, the presence/absence of a target substance in a sample can be determined more accurately and more rapidly by using the probe array. Similarly, the structure of a target substance in a sample can be identified more accurately and more rapidly using the probe array.

According to the present invention, some degrees of offset positioning during supply of at least one of a probe solution and a sample solution to a solid support can also be settled by using a solid support having wells on the surface of the solid support. A further increase in accuracy in the detection of a target substance and the identification of its structure can be achieved by providing a matrix with various functions.

[SEQ ID List]
  SEQ ID NO: 1
  SEQUENCE LENGTH: 18

---

What is claimed is:

1. A method of spotting to a solid support a probe which can bind specifically to a target comprising the steps of:

providing a solid support having a first functional epoxy group on the surface thereof by applying to the solid support polyglycidyl methacrylate having an epoxy group;

providing a single-stranded nucleic acid probe having a second functional amino group;

supplying and attaching a liquid containing the single-stranded nucleic acid probe on a selected portion of the surface of the solid support; and forming a spot of the probe on the surface of the solid support.

2. A method of spotting a probe which can bind specifically to a target to a solid support comprising the steps of:

supplying and attaching a liquid containing a single-stranded nucleic acid probe on a selected portion of the surface of said solid support; and forming a spot of the probe on the surface of the solid support, wherein the liquid contains urea at 5–10 wt %, glycerine at 5–10 wt %, thiodiglycol at 5–10 wt %, and an acetylene alcohol at 0.5–1 wt %, wherein each said weight % is based on the total weight of the liquid.

3. The method according to claim 2, wherein the acetylene alcohol has a structure represented by the following general formula (I):

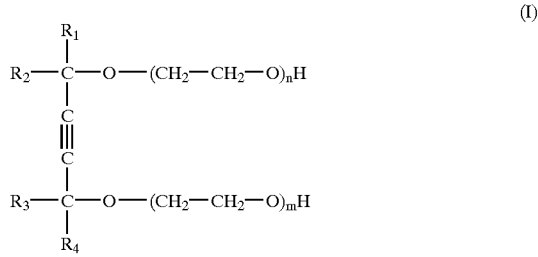

wherein $R_1$, $R_2$, $R_3$ and $R_4$ are each an alkyl group, each m and n represents an integer, and m=0 and n=0 or $1 \leq m+n \leq 30$, and when m+n=1, m or n is 0.

4. A method of manufacturing a probe array having a plurality of spots arranged independently at a plurality of sites on a surface of a solid support, the spots containing a probe which can bind specifically to a target substance, comprising the steps of:

providing a solid support having a first functional epoxy group on the surface thereof;

providing a single-stranded nucleic acid probe having a second functional amino group which reacts with the first functional epoxy group upon contact;

ejecting droplets of a liquid containing the single-stranded nucleic acid probe to selected different spot sites on the surface of said solid support, wherein the epoxy group is introduced by applying polyglycidyl methacrylate having an epoxy group to the solid support.

5. A method of manufacturing a probe array having a plurality of spots arranged independently at a plurality of sites on a surface of a solid support, the spots containing a probe which can bind specifically to a target substance, comprising the steps of:

supplying and attaching a liquid containing a single-stranded nucleic acid probe on a selected portion of the surface of the solid support; and forming spots of the probe at predetermined sites on the surface of the solid support, wherein the liquid contains urea at 5–10 wt %, glycerine at 5–10 wt %, thiodiglycol at 5–10 wt %, and an acetylene alcohol at 0.5–1 wt %, each said wt % based on the total weight of the liquid.

6. The method according to claim 5, wherein the acetylene alcohol has a structure represented by the following general formula (I):

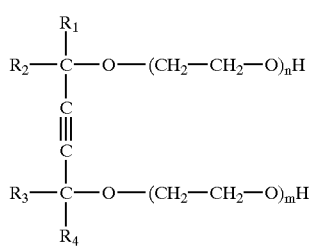

wherein $R_1$, $R_2$, $R_3$ and $R_4$ are each an alkyl group, each m and n represents an integer, and m=0 and n=0 or $1 \leq m+n \leq 30$, and when m+n=1, m or n is 0.

7. A method of manufacturing a probe array having a plurality of spots arranged independently at a plurality of sites on a surface of a solid support, the spots containing a probe which can bind specifically to a target substance, comprising the steps of:

(a) providing a solid support having a surface partitioned by a matrix arranged in a pattern on the surface and having a plurality of wells, the surface of the solid support being exposed at a bottom of the well;

(b) supplying and attaching a liquid containing the probe in the respective wells by ejecting the liquid; and (c) forming spots of the probe in the respective wells;

wherein the matrix pattern is formed by photolithography, wherein the photolithography comprises the steps of forming a photosensitive resin layer on the surface of the solid support, exposing the photosensitive resin layer to light in a pattern corresponding to the matrix pattern, and developing; and wherein the photosensitive resin layer is a UV resist selected from the group consisting of a cyclized polyisoprene-aromatic bisazide resist, a phenol resin-aromatic azide compound resist and a novolak resin-diazonaphtoquinone resist.

8. A method of manufacturing a probe array having a plurality of sites on a surface of a solid support, the spots containing a probe which can bind specifically to a target substance, comprising the steps of:

(a) providing a solid support having a surface partitioned by a matrix arranged in a pattern on the surface and having a plurality of wells, the surface of the solid support being exposed at a bottom of the well;

(b) supplying and attaching a liquid containing the probe in the respective wells by ejecting the liquid; and (c) forming spots of the probe in the respective wells;

wherein the matrix pattern is formed by photolithography, said photolithography comprises the steps of forming a photosensitive resin layer on the surface of the solid support, exposing the photosensitive resin layer to light in a pattern corresponding to the matrix pattern, and developing, wherein the photosensitive resin layer is a DEEP-UV resist, wherein the DEEP-UV resist is a radiolysable polymer resist or a dissolution suppressant resist.

9. The method of manufacturing according to claim 8, wherein the radiolysable polymer resist is at least one selected from the group consisting of polymethyl methacrylate, polymethylene sulfone, polyhexafluorobutyl methacrylate, polymethylisopropenyl ketone, and poly-1-trimethylsilyl propyne bromide.

10. The method of manufacturing according to claim 8, wherein the dissolution suppressant resist is o-nitrobenzyl cholate ester.

11. A method of manufacturing a probe array having a plurality of spots arranged independently at a plurality of sites on a surface of a solid support, the spots containing a probe which can bind specifically to a target substance, comprising the steps of:

(a) providing a solid support having a surface partitioned by a matrix arranged in a pattern on the surface and having a plurality of wells, the surface of the solid support being exposed at a bottom of the well;

(b) supplying and attaching a liquid containing the probe in the respective wells by ejecting the liquid; and (c) forming spots of the probe in the respective wells, wherein the matrix pattern is formed by photolithography, said photolithography comprises the steps of forming a photosensitive resin layer on the surface of the solid support, exposing the photosensitive resin layer to light in a pattern corresponding to the matrix pattern, and developing, wherein the photosensitive resin layer is a polyvinylphenol-3,3'-diazidediphenyl sulfone or polyglycidyl polymethacrylate DEEP-UV resist.

12. A method of manufacturing a probe array having a plurality of spots arranged independently at a plurality of sites on a surface of a solid support, the spots containing a probe which can bind specifically to a target substance, comprising the steps of:

(a) providing a solid support having a surface partitioned by a matrix arranged in a pattern on the surface and having a plurality of wells, the surface of the solid support being exposed at a bottom of the well;

(b) supplying and attaching a liquid containing the probe in the respective wells by ejecting the liquid; and (c) forming spots of the probe in the respective wells, wherein the matrix pattern is formed by photolithography, said photolithography comprises the steps of forming a photosensitive resin layer on the surface of the solid support, exposing the photosensitive resin layer to light in a pattern corresponding to the matrix pattern, and developing, wherein water repellency of the matrix pattern is further improved by postbaking of the matrix pattern.

13. A method of manufacturing a probe array having a plurality of spots arranged independently at a plurality of sites on a surface of a solid support, each spot containing a probe, comprising the steps of:

provided a solid support having a maleimido group derived from N-(6-maleimidocaproyloxy) succinimide on the surface thereof, providing a nucleic acid probe having a thiol group which reacts with the maleimido group upon contact; and ejecting droplets of a liquid of the nucleic acid probe having the thiol group onto the sites having the maleimido group, wherein the liquid contains urea at 5–10 wt %, glycerine at 5–10 wt %, thiodiglycol at 5–10 wt %, and an acetylene alcohol at 0.5–1 wt % based on the total weight of the liquid.

14. The method according to claim 13, wherein the acetylene alcohol has a structure represented by the following general formula (I):

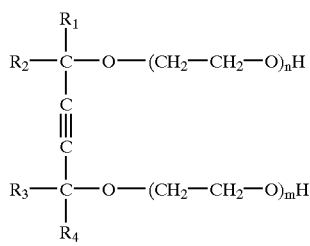

(I)

wherein $R_1$, $R_2$, $R_3$ and $R_4$ independently represent an alkyl group, m and n independently represent an integer, and $0 \leq m+n \leq 30$.

15. A method of manufacturing a probe array having a plurality of spots arranged independently at a plurality of sites on a surface of a solid support, the spots containing a probe which can bind specifically to a target substance, comprising the steps of:

(a) providing a probe having a thiol group;

(b) providing a solid support having maleimido groups on its entire surface, each maleimido group being an active site capable of reacting with a thiol group; and (c) ejecting droplets of a liquid containing the probe of step (a) on the solid support resulting from the step (b) wherein the liquid contains urea at 5–10 wt %, glycerine at 5–10 wt %, thiodiglycol at 5–10 wt %, and an acetylene alcohol at 0.5–1 wt %, based on the total weight of the liquid.

16. The method according to claim 15, wherein the acetylene alcohol has a structure represented by the following general formula (I):

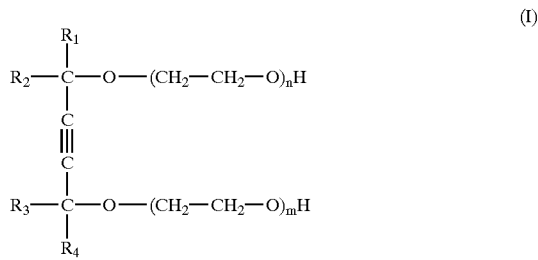

(I)

wherein $R_1$, $R_2$, $R_3$ and $R_4$ independently represent an alkyl group, m and n independently represent an integer, and $0 \leq m+n \leq 30$.

* * * * *

UNITED STATES PATENT AND TRADEMARK OFFICE
CERTIFICATE OF CORRECTION

PATENT NO. : 6,476,215 B1
DATED : November 5, 2002
INVENTOR(S) : Tadashi Okamoto et al.

It is certified that error appears in the above-identified patent and that said Letters Patent is hereby corrected as shown below:

<u>Title page,</u>
Item [56], OTHER PUBLICATIONS,
4th reference, "pp. 130-1135." should read -- pp. 1130-1135. --;
5th reference, "Methof For Antgen"." should read -- Method for Antigen". --; and
"O'Donnel-Maloney, et al.," should read -- O'Donnell-Maloney, et al., --

<u>Column 1,</u>
Line 54, "to" should be deleted; and
Line 56, "is a" should read -- is --.

<u>Column 2,</u>
Line 15, "other" should read -- another --;
Line 21, "provided is" should read -- is provided --; and
Lines 30, 37, 49 and 61, "provided is" should read -- there is provided --.

<u>Column 3,</u>
Lines 34, 45 and 64, "cross sectional" should read -- cross-sectional --; and
Line 60, "heads," should read -- head --.

<u>Column 5,</u>
Line 13, "alkyl," should read -- alkyl --.

<u>Column 6,</u>
Line 23, "an" should be deleted; and
Line 51, "thiol," should read -- thiol --.

<u>Column 7,</u>
Line 40, "Nest," should read -- Next, --; and
Line 56, "used," should read -- used --.

<u>Column 8,</u>
Line 2, "a way" should read -- away --; and
Line 32, "a" should read -- as --.

<u>Column 10,</u>
Line 5, "react each other into" should read -- react at --; and
Line 13, "5-terminus" should read -- 5'-terminus --.

UNITED STATES PATENT AND TRADEMARK OFFICE
CERTIFICATE OF CORRECTION

PATENT NO. : 6,476,215 B1
DATED : November 5, 2002
INVENTOR(S) : Tadashi Okamoto et al.

It is certified that error appears in the above-identified patent and that said Letters Patent is hereby corrected as shown below:

Column 11,
Line 23, "cross sectional" should read -- cross-sectional --;
Line 26, "are arranged" should read -- is --;
Line 27, "in a form of a matrix are" should be deleted.
Line 40, "florescence" should read -- fluorescence --; and
Line 67, "such benzyl," should be deleted.

Column 14,
Line 31, "desirable" should read -- desirable that --.

Column 15,
Line 4, "an" should read -- a --;
Line 11, "cases," should read -- case, --; and
Line 51, "proceed" should read -- promote --.

Column 17,
Line 44, "proceed" should read -- promote --.

Column 21,
Line 1, "HPLC, and" should read -- HPLC in order to determine --.

Column 22,
Lines 15 and 26, "proceed" should read -- promote --; and
Line 65, "bee" should read -- been --.

Column 24,
Line 43, "prove" should read -- probe --.

Column 25,
Line 48, "remained" should read -- remaining --.

UNITED STATES PATENT AND TRADEMARK OFFICE
CERTIFICATE OF CORRECTION

PATENT NO. : 6,476,215 B1
DATED : November 5, 2002
INVENTOR(S) : Tadashi Okamoto et al.

It is certified that error appears in the above-identified patent and that said Letters Patent is hereby corrected as shown below:

Column 27,
Line 41, "Is" should read -- is --; and
Line 54, "left standing" should read -- being allowed to stand --.

Column 28,
Line 49, "remained" should read -- remaining --.

Column 29,
Line 30, "absolution" should read -- a solution --.

Signed and Sealed this

Twenty-sixth Day of August, 2003

JAMES E. ROGAN
*Director of the United States Patent and Trademark Office*

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Thiol group bound at the 5'-terminus

<400> SEQUENCE: 1
acattttgct gccggtca                                                 18

<210> SEQ ID NO 2
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Thiol group bound at the 5'-terminus

<400> SEQUENCE: 2
acattttgtt gccggtca                                                 18

<210> SEQ ID NO 3
<211> LENGTH: 18
<212> TYPE: DNA
<213> ORGANISM: Artificial Sequence
<220> FEATURE:
<221> NAME/KEY:
<222> LOCATION:
<223> OTHER INFORMATION: Synthetic

<400> SEQUENCE: 3
actggccgct tttttaca                                                 18

<210> SEQ ID NO 4
<211> LENGTH: 18
<212> TYPE: DNA
<213> ORGANISM: Artificial Sequence
<220> FEATURE:
<221> NAME/KEY:
<222> LOCATION:
<223> OTHER INFORMATION: Synthetic

<400> SEQUENCE: 4
actggcatct tgtttaca                                                 18

<210> SEQ ID NO 5
<211> LENGTH: 12
<212> TYPE: DNA
<213> ORGANISM: Artificial Sequence
<220> FEATURE:
<221> NAME/KEY:
<222> LOCATION:
<223> OTHER INFORMATION: Synthetic

<400> SEQUENCE: 5
gcctgatcag gc                                                       12
```

```
<210> SEQ ID NO 6
<211> LENGTH: 10
<212> TYPE: DNA
<213> ORGANISM: Artificial Sequence
<220> FEATURE:
<221> NAME/KEY:
<222> LOCATION:
<223> OTHER INFORMATION: Synthetic

<400> SEQUENCE: 6
aaaaaaaaaa                                                           10

<210> SEQ ID NO 7
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Cysteine residue bound at the N'-terminus

<400> SEQUENCE: 7
actggccgtc gttttaca                                                  18

<210> SEQ ID NO 8
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Cysteine residue bound at the N'-terminus

<400> SEQUENCE: 8
actggccgtt gttttaca                                                  18

<210> SEQ ID NO 9
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Amino group bound at the 5'-terminus

<400> SEQUENCE: 9
tgaccggcag caaaatgt                                                  18

<210> SEQ ID NO 10
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Amino group bound at the 5'-terminus

<400> SEQUENCE: 10
tgaccggcac caaaatgt                                                  18

<210> SEQ ID NO 11
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Amino group bound at the 5'-terminus
```

-continued

```
<400> SEQUENCE: 11
tgacccgcac caatatgt                                                  18

<210> SEQ ID NO 12
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Thiol group bound at the 5'-terminus

<400> SEQUENCE: 12
tgacccgcag caaaatgt                                                  18

<210> SEQ ID NO 13
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Thiol group bound at the 5'-terminus

<400> SEQUENCE: 13
tgaccggcac caaaatgt                                                  18

<210> SEQ ID NO 14
<211> LENGTH: 18
<212> TYPE: DNA
<213> ORGANISM: Artificial Sequence
<220> FEATURE:
<221> NAME/KEY: modified_base
<222> LOCATION: 1
<223> OTHER INFORMATION: Thiol group bound at the 5'-terminus

<400> SEQUENCE: 14 tgaccgcac caatatgt                                                   18
```